(12) United States Patent
Takahashi et al.

(10) Patent No.: US 12,426,579 B2
(45) Date of Patent: Sep. 30, 2025

(54) IMMUNODEFICIENT MOUSE

(71) Applicant: Central Institute for Experimental Animals, Kanagawa (JP)

(72) Inventors: Takeshi Takahashi, Kanagawa (JP); Ikumi Katano, Kanagawa (JP)

(73) Assignee: Central Institute for Experimental Animals, Kanagawa (JP)

( * ) Notice: Subject to any disclaimer, the term of this patent is extended or adjusted under 35 U.S.C. 154(b) by 1187 days.

(21) Appl. No.: 17/251,272

(22) PCT Filed: Sep. 25, 2019

(86) PCT No.: PCT/JP2019/037675
§ 371 (c)(1),
(2) Date: Dec. 11, 2020

(87) PCT Pub. No.: WO2020/067199
PCT Pub. Date: Apr. 2, 2020

(65) Prior Publication Data
US 2021/0259221 A1    Aug. 26, 2021

(30) Foreign Application Priority Data

Sep. 27, 2018 (JP) ................ 2018-181930
Nov. 20, 2018 (JP) ................ 2018-217229

(51) Int. Cl.
*A01K 67/027* (2024.01)
*A01K 67/0276* (2024.01)
*A01K 67/0278* (2024.01)

(52) U.S. Cl.
CPC ...... *A01K 67/0278* (2013.01); *A01K 67/0276* (2013.01); *A01K 2207/12* (2013.01); *A01K 2207/15* (2013.01); *A01K 2217/075* (2013.01); *A01K 2227/105* (2013.01); *A01K 2267/0387* (2013.01)

(58) Field of Classification Search
CPC ................................ A01K 67/0278
See application file for complete search history.

(56) References Cited

U.S. PATENT DOCUMENTS

2003/0182671 A1    9/2003  Ito et al.

FOREIGN PATENT DOCUMENTS

| JP | 3753321 B2 | 3/2006 |
| WO | 2011084664 A1 | 7/2011 |
| WO | 2017118675 A1 | 7/2017 |

OTHER PUBLICATIONS

Bankert et al., PLoS ONE. 2011; 6(9): e24420. p. 1-9. (Year: 2011).*
Jackson Laboratory Strain # 028615, available in 2016. Strain description is downloaded from https://www.jax.org/strain/028615, downloaded on May 21, 2024, p. 1-11. (Year: 2016).*
Shultz et al., J Immunol. 2005; 174(10): 6477-6489. (Year: 2005).*
Li et al. Inhibitory Fcg Receptor Engagement Drives Adjuvant and Anti-Tumor Activities of Agonistic CD40 Antibodies. Science. 2011;333:1030-1034. (Year: 2011).*
Bournazos Stylianos et al: "Broadly Neutralizing Anti-HIV-1 Antibodies Require Fc Effector Functions for In Vivo Activity", Cell, Elsevier, Amsterdam NL, vol. 158, No. 6, Sep. 11, 2014 (Sep. 11, 2014), pp. 1243-1253, XP029055523, ISSN: 0092-8674, DOI: 10.1016/J.CELL.2014.08.023.
European Office Action, issued Feb. 2, 2023 (6 pages).
Zhou, Qianjun, et al. "Humanized Nod-SCID IL2RG −/− Mice as a Preclinical Model for Cancer Research and Its Potential Use for Individualized Cancer Therapies." Cancer Letters, vol. 344, No. 1, Oct. 31, 2013, pp. 13-19., https://doi.org/10.1016/j.canlet.2013.10.015.
Clynes, Raphael A., et al. "Inhibitory FC Receptors Modulate in Vivo Cytoxicity against Tumor Targets." Nature Medicine, vol. 6, No. 4, Apr. 1, 2000, pp. 443-446., https://doi.org/10.1038/74704.
Katano, Ikumi, et al. "Long-Term Maintenance of Peripheral Blood Derived Human NK Cells in a Novel Human IL-15-Transgenic Nog Mouse." Scientific Reports, vol. 7, No. 1, Dec. 1, 2017, https://doi.org/10.1038/s41598-017-17442-7.
Schwab, Inessa, et al. "Pathways Responsible for Human Autoantibody and Therapeutic Intravenous IgG Activity in Humanized Mice." Cell Reports, vol. 13, No. 3, Oct. 20, 2015, https://doi.org/10.1016/j.celrep.2015.09.013.
Extended European Search Report, EP Application No. 19866903.8, mailed Jan. 4, 2022 (9 pages).
Chinese Office Action, CN Application No. 201980005541.4, mailed Jan. 27, 2022 (13 pages).
Kumi Katano et al., "Abstract LB-032: NOG-FcgR KO hIL-15 Tg mice provide a highly sensitive assay system for ADCC activity of human NK cells", Cancer Research, vol. 79, Issue 13, supplement, Jul. 2019, pp. LB-032, DOI:10.1158/1538-7445.AM2019-LB-032.
International Search Report, PCT Application No. PCT/JP2019/037675, mailed Dec. 3, 2019 (4 pages).
Chen, Dan, et al. Comparison of three methods of separating human peripheral blood monocytes, Nov. 6, 2014, Journal of Tianjin Medical University, vol. 20, No. 6.
Chinese Office Action, Jul. 19, 2022 (6 Pages).

(Continued)

*Primary Examiner* — Taeyoon Kim
*Assistant Examiner* — Jianjian Zhu
(74) *Attorney, Agent, or Firm* — Occhiuti & Rohlicek LLP

(57) ABSTRACT

An object of the present invention is to provide an immunodeficient mouse which is capable of eliminating effects of immune cells from the immunodeficient mouse against human antibodies and in which human cells are engrafted at high level.
Deletion of a mouse FcgR gene from an NOG mouse results in a mouse that does not exhibit antibody-dependent cellular cytotoxic activity on tumors, and in the mouse, human cells can be engrafted at significantly higher level than that in the NOG mouse. Furthermore, by introducing the human IL-15 gene into the mouse and engrafting a human NK cell in the mouse, only human NK cells become effector cells to enable evaluation of ADCC activity.

18 Claims, 16 Drawing Sheets
Specification includes a Sequence Listing.

(56) References Cited

OTHER PUBLICATIONS

Lux, Anja et al., "A Humanized Mouse Identifies the Bone Marrow as a Niche with Low Therapeutic IgG Activity", Cell Reports, vol. 7, No. 1, Apr. 10, 2014, pp. 236-248.
White, Ann L. et al. "Fc γ Receptor Dependency of Agonistic CD40 Antibody in Lymphoma Therapy Can Be Overcome through Antibody Multimerization", The Journal of Immunology, vol. 193, No. 4, 2014, pp. 1828-1835, www.jimmunol.org/cgi/doi/10.4049/jimmunol.1303204.

* cited by examiner

[Fig. 1]
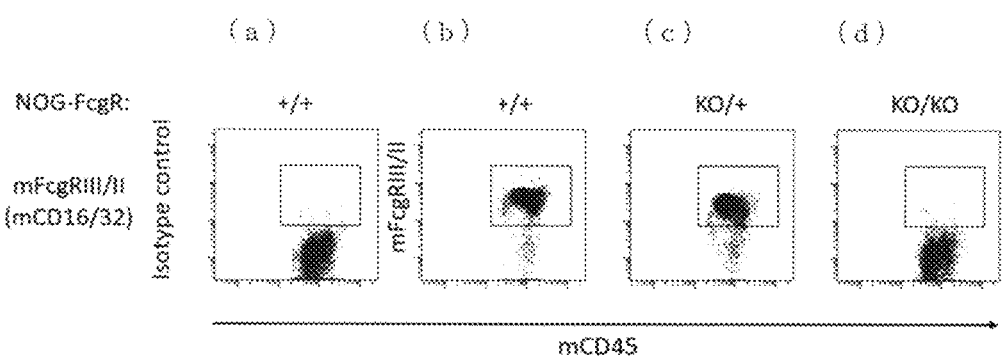
[Fig. 2]
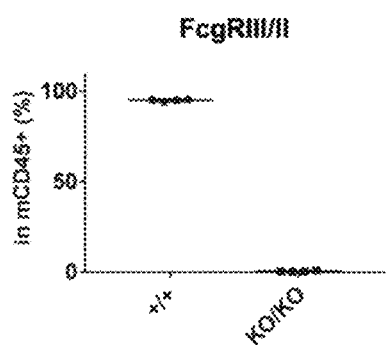

[Fig. 3]
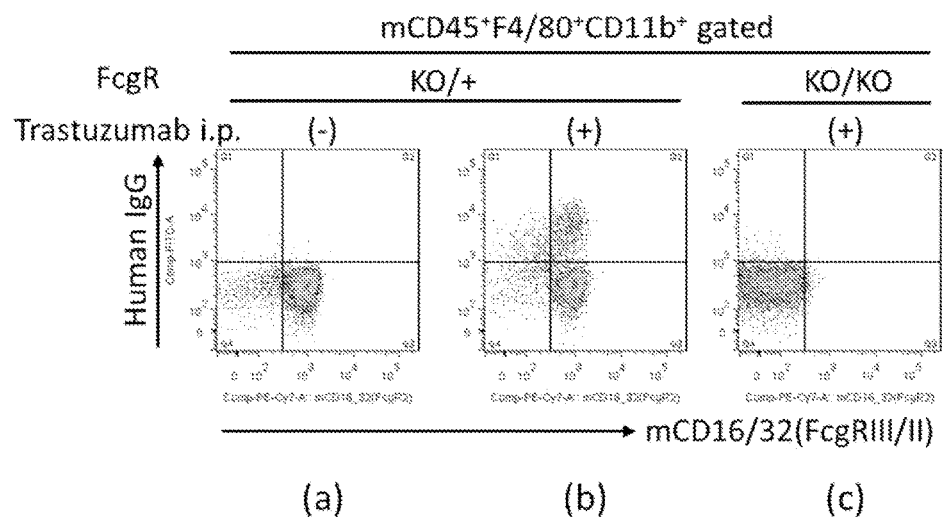
[Fig. 4]
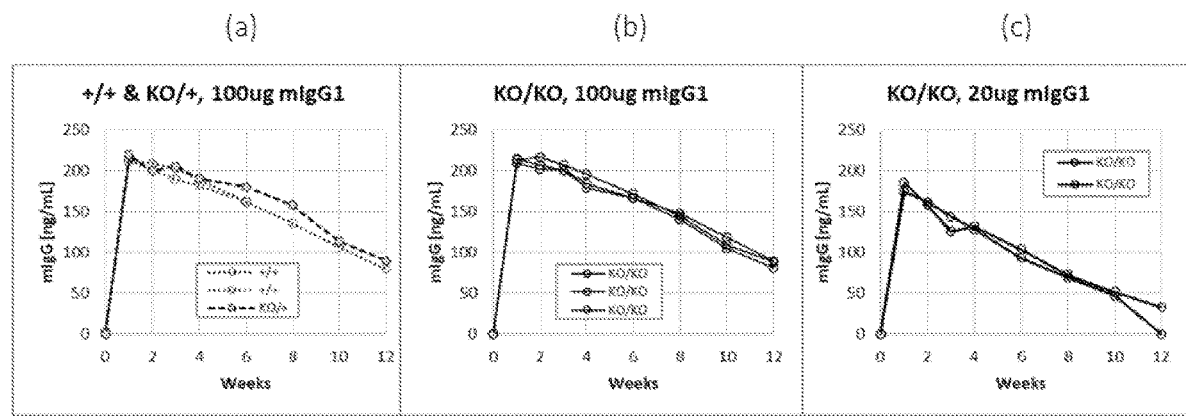

[Fig. 5]
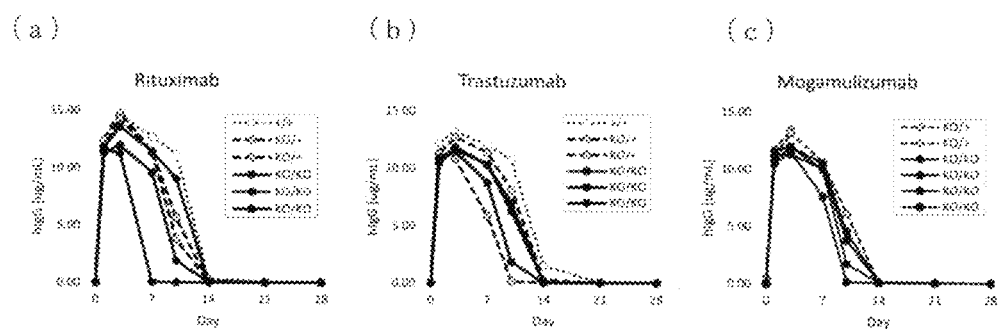
[Fig. 6]
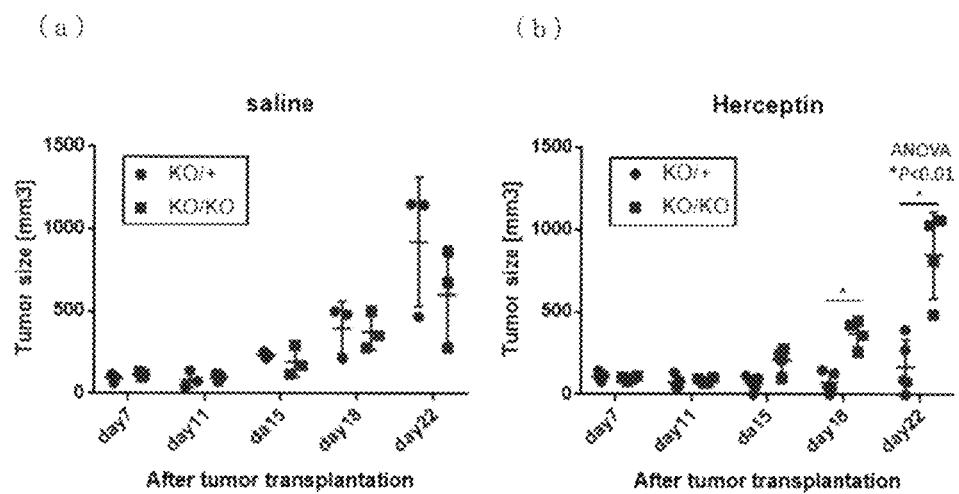

[Fig. 7]
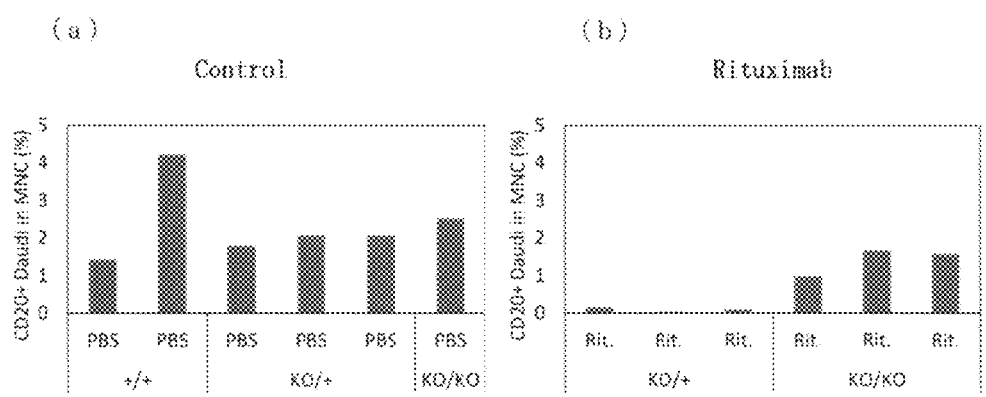

[Fig. 8]
(a)
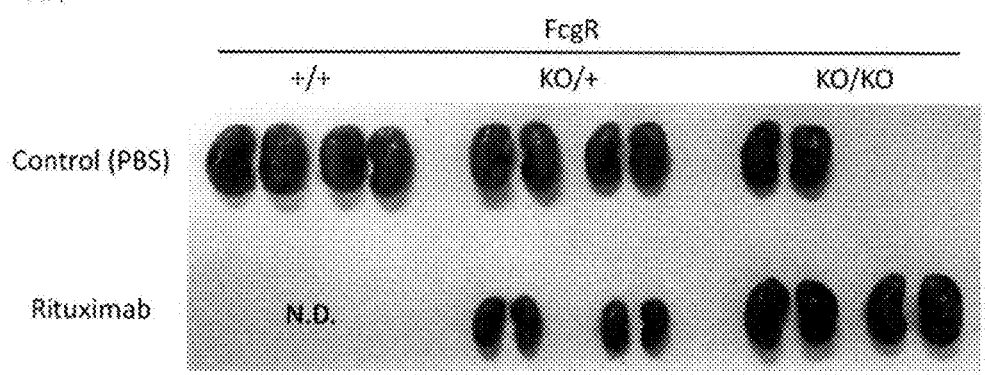
(b)
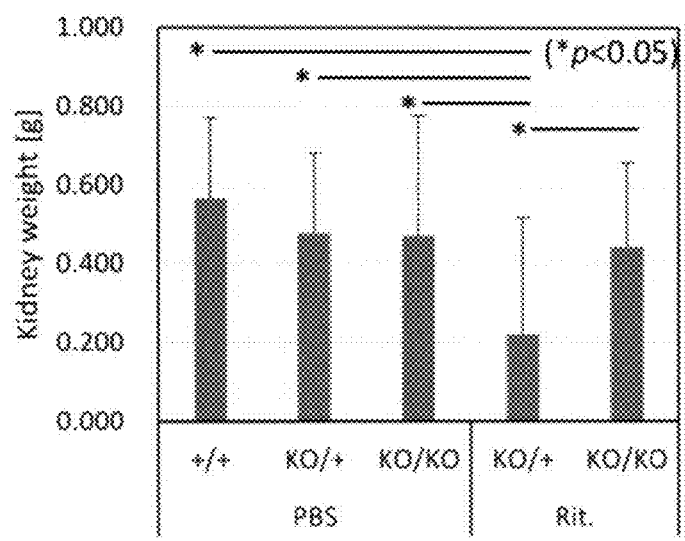

[Fig. 9]
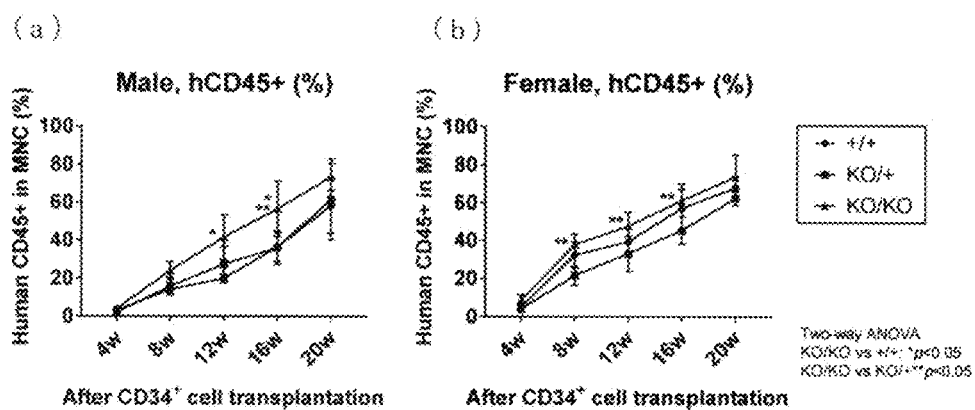
[Fig. 10]
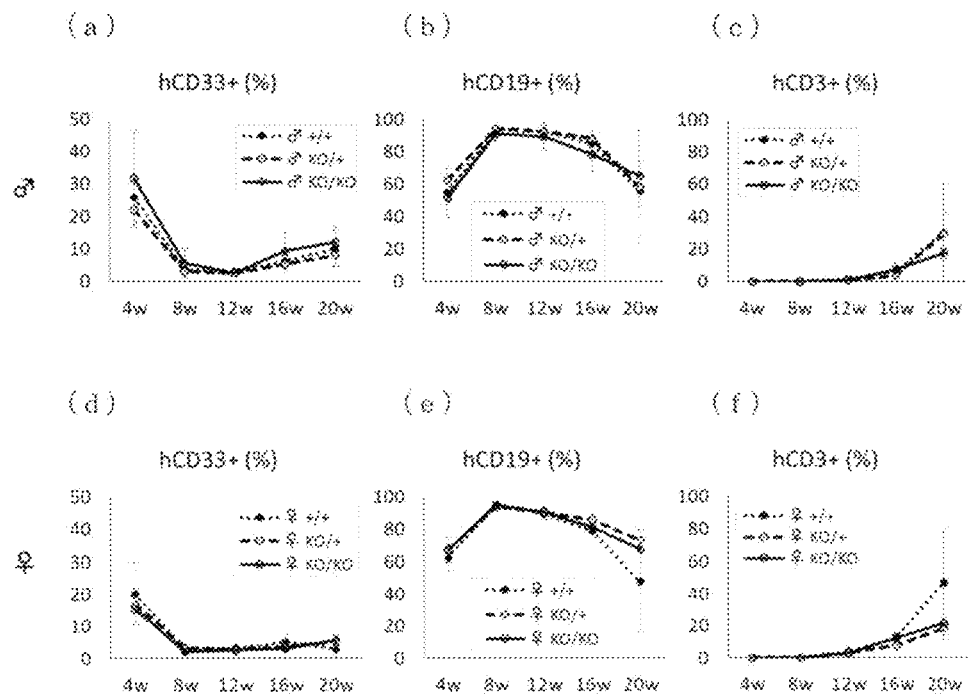

[Fig. 11]
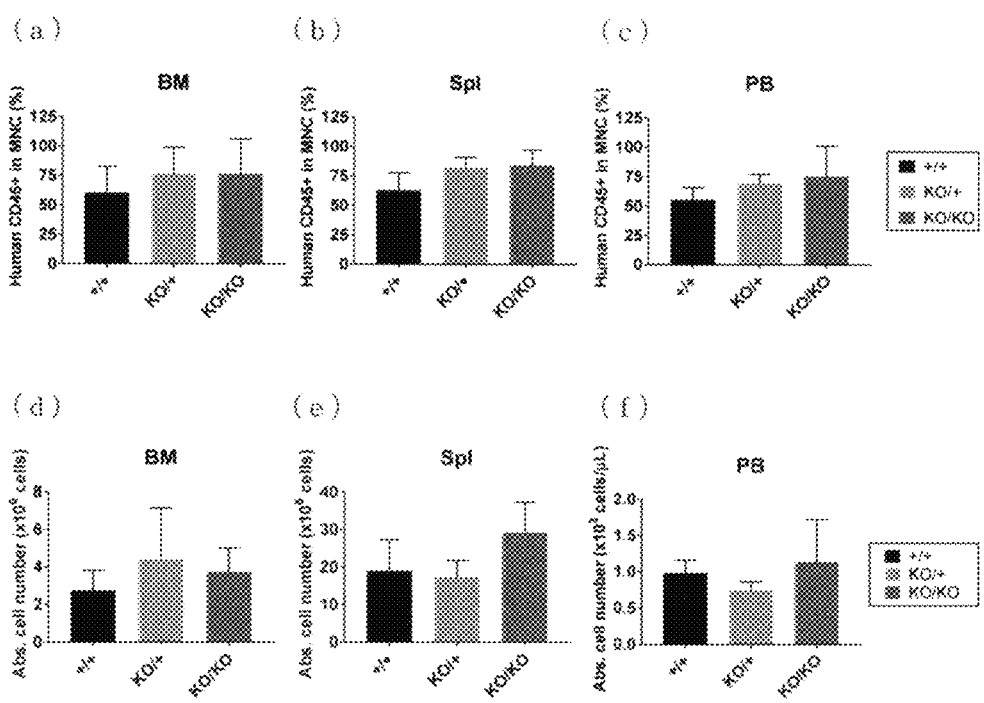

[Fig. 12]
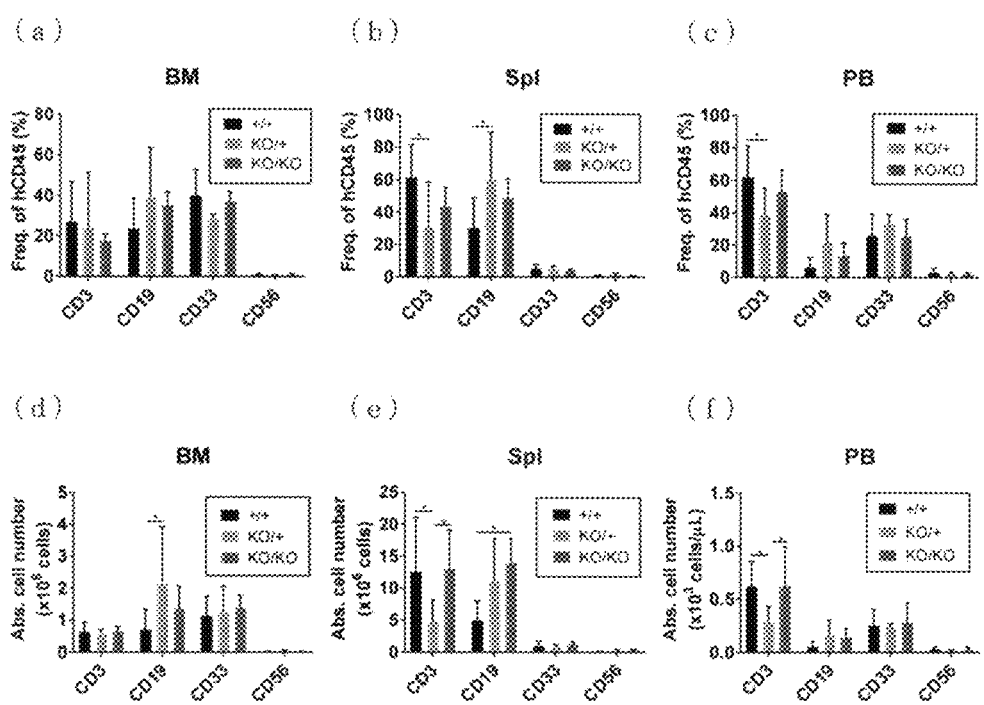

[Fig. 13]
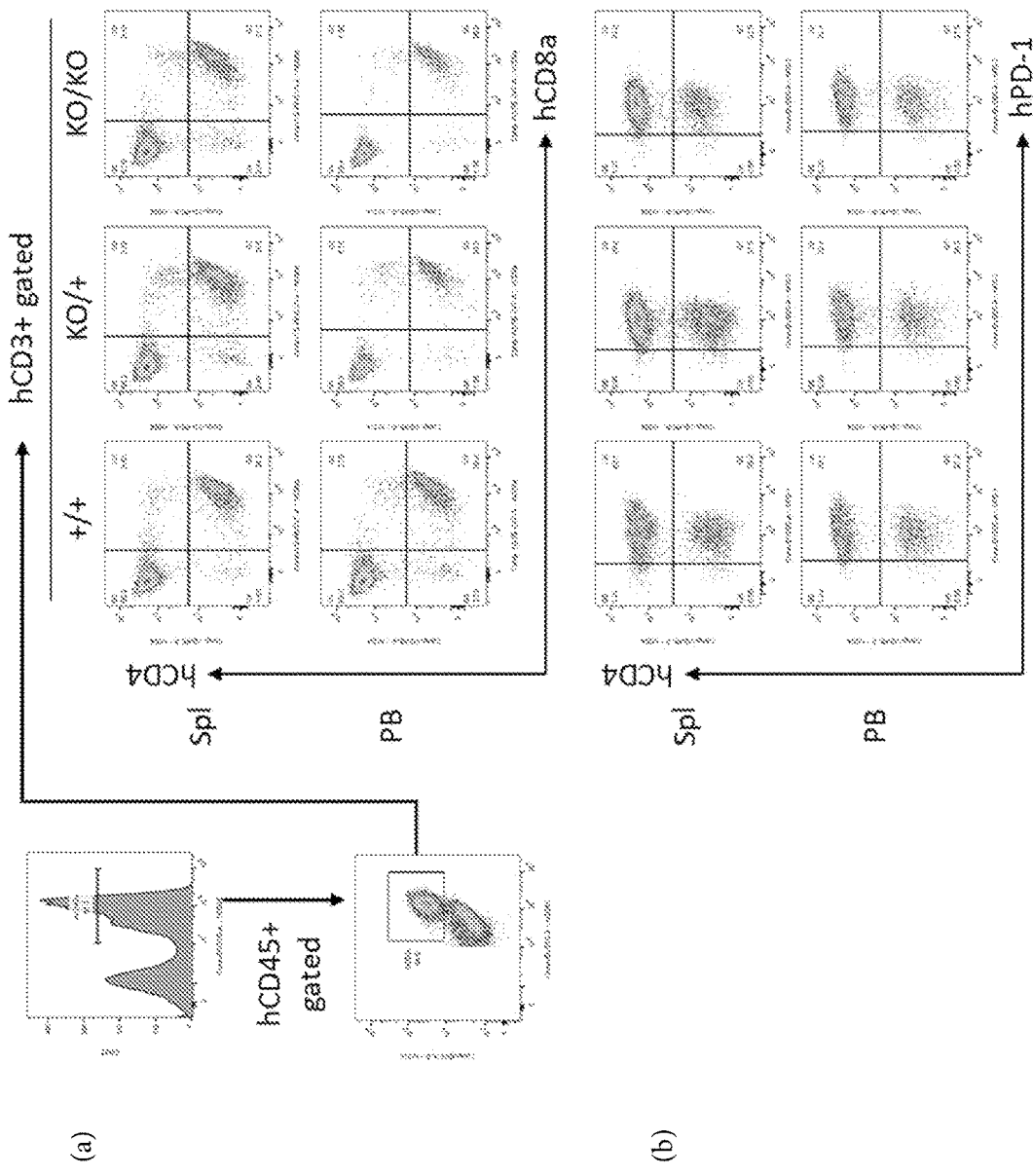

[Fig. 14]
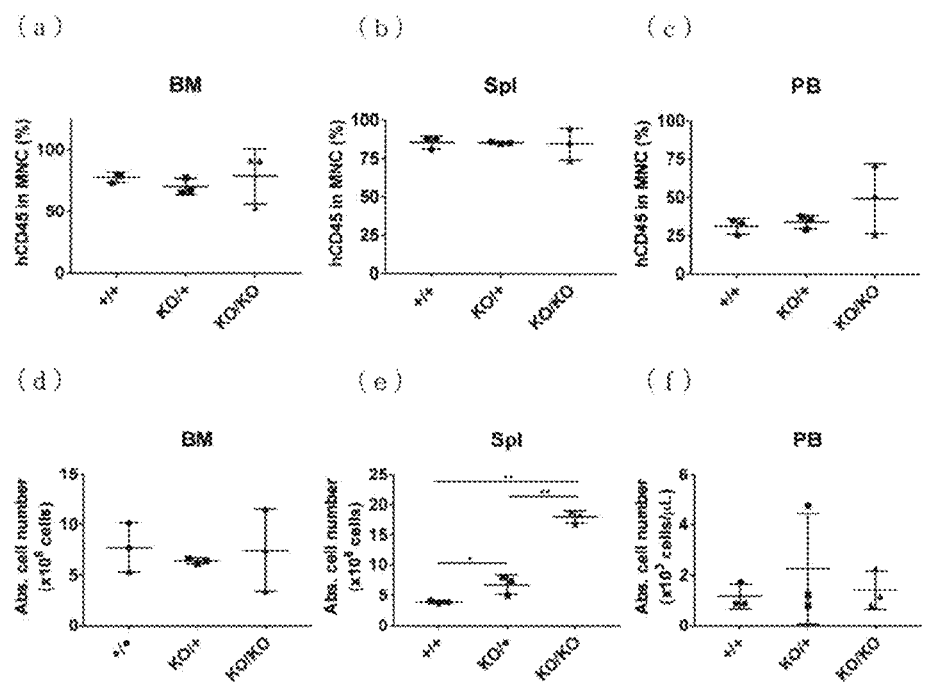

[Fig. 15]
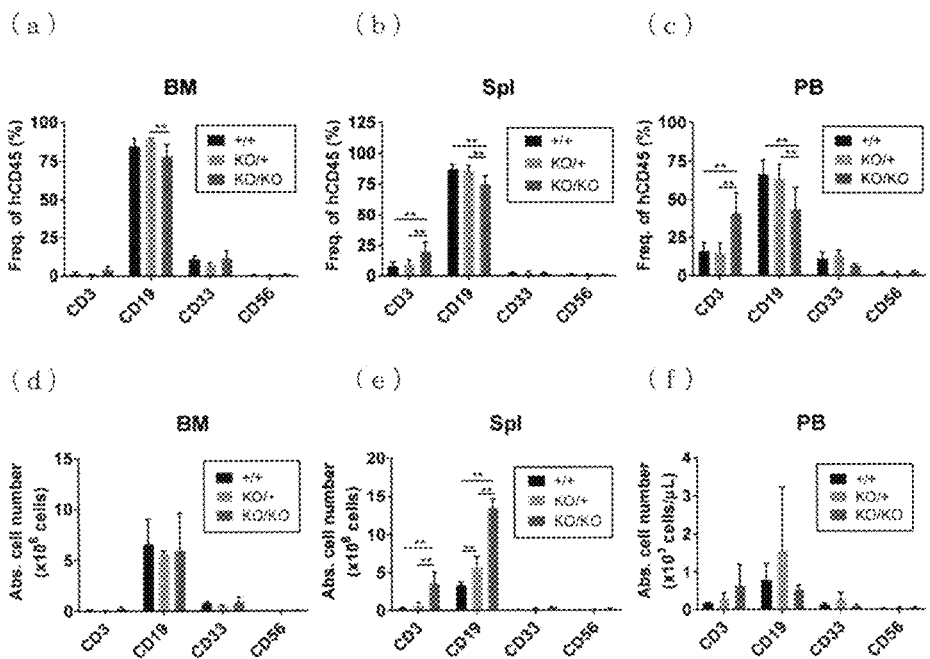
[Fig. 16]
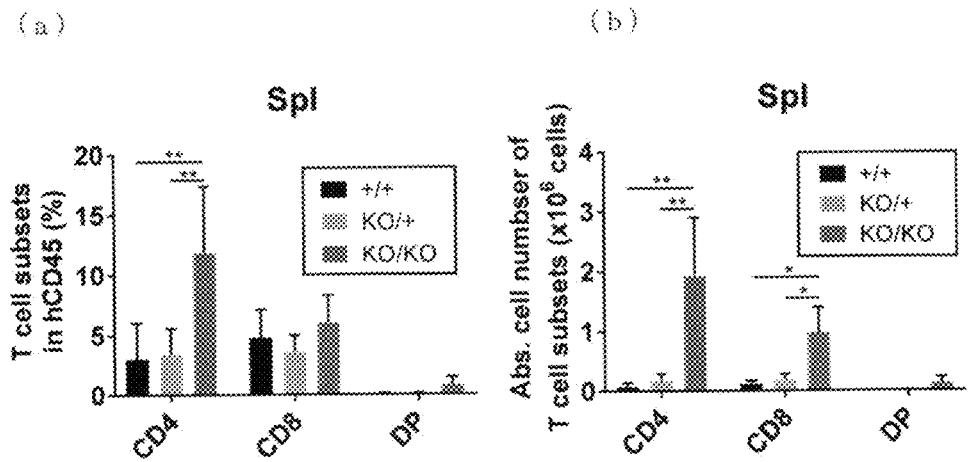

[Fig. 17]
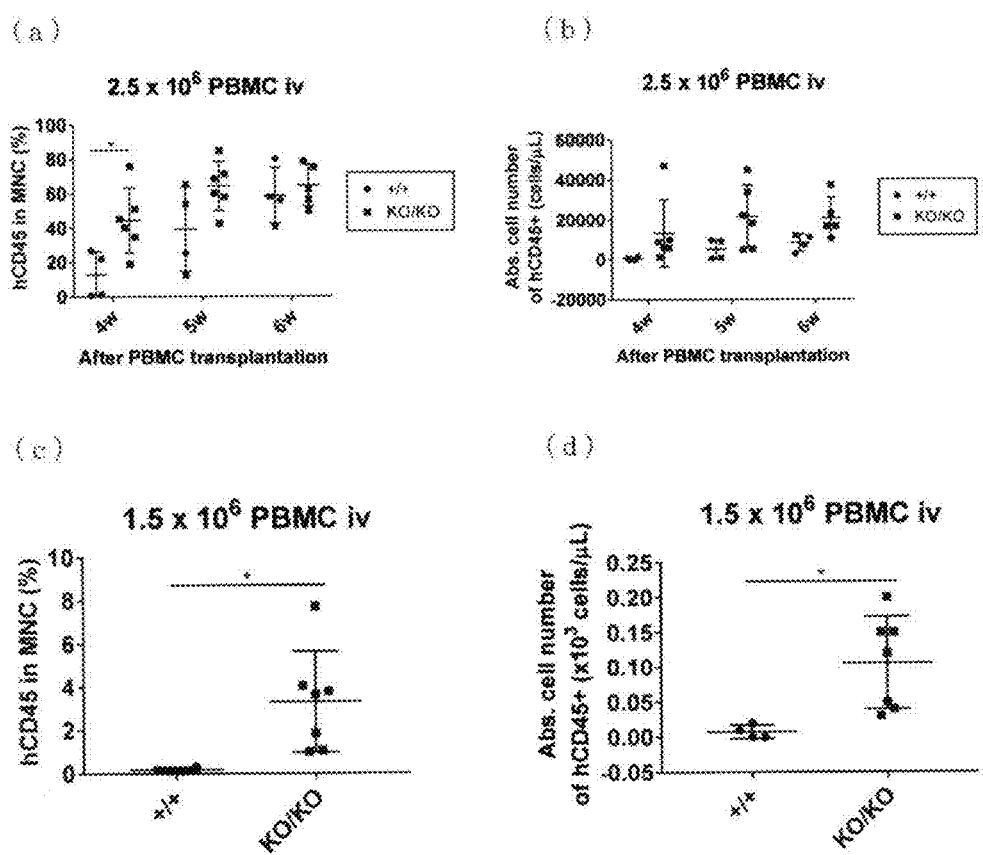

[Fig. 18]
(a) 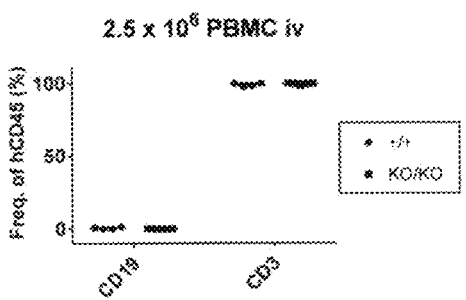
(b) 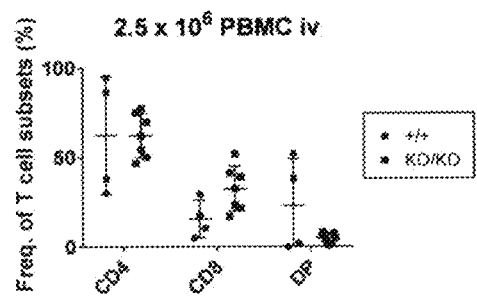
(c) 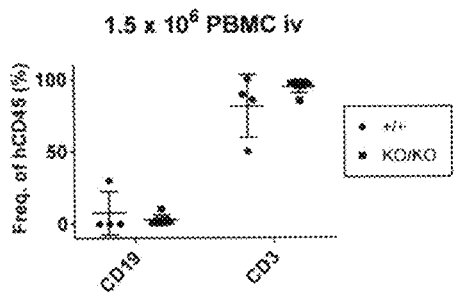
(d) 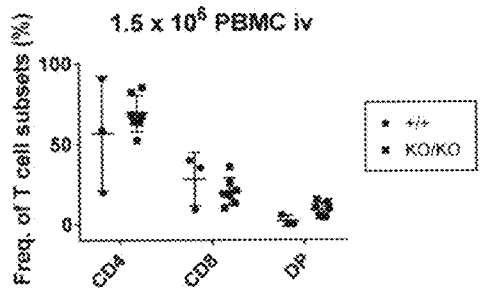

[Fig. 19]
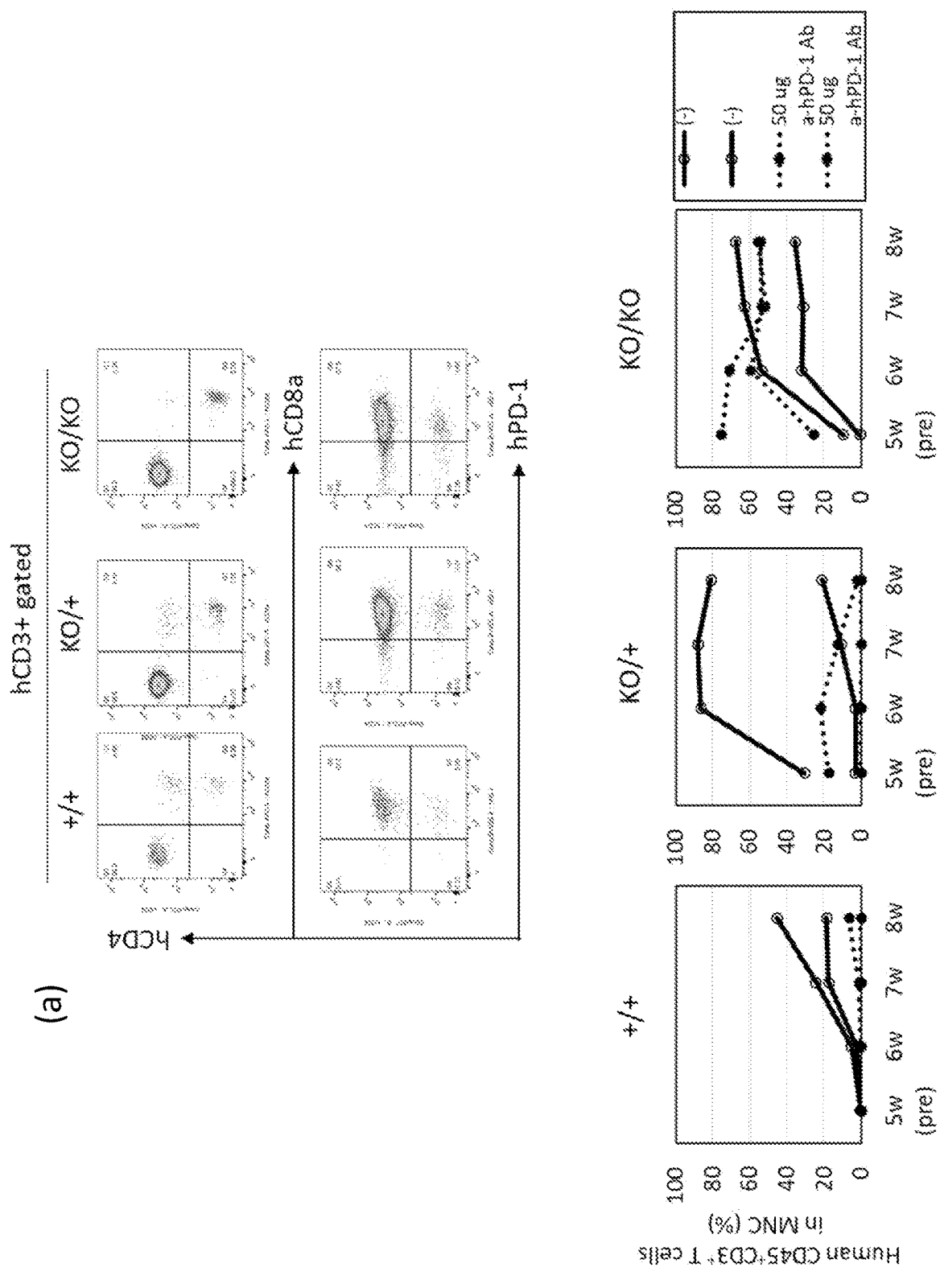

[Fig. 20]
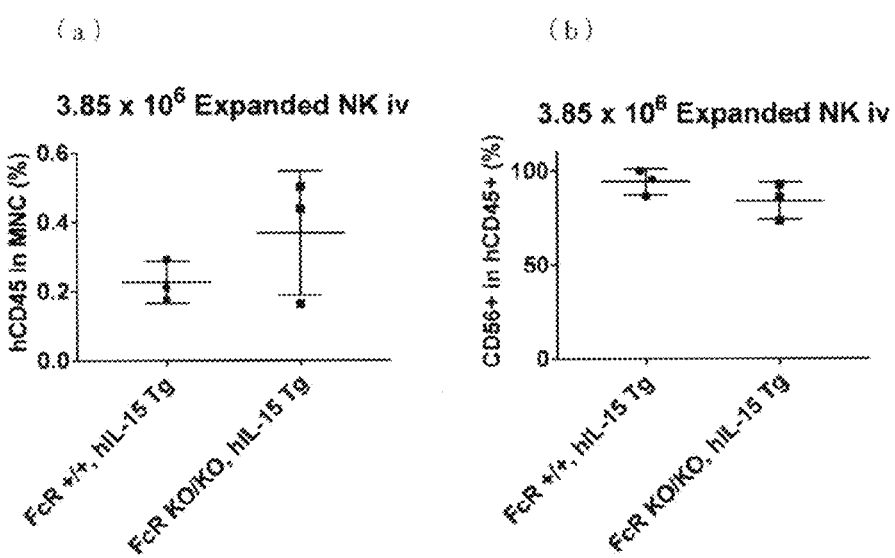
[Fig. 21]
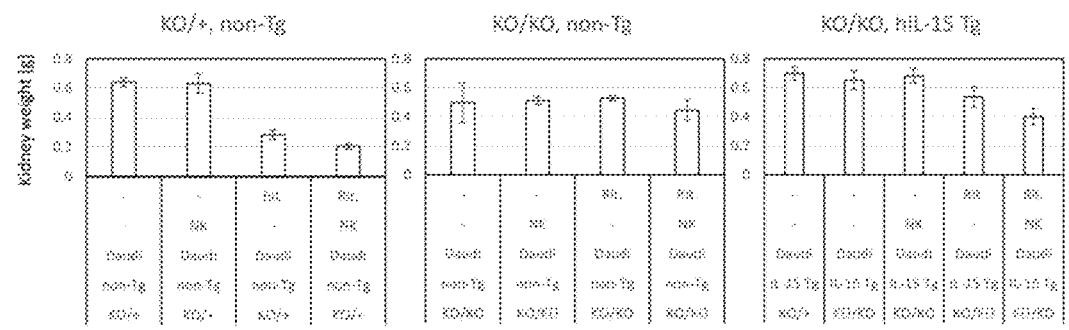

[Fig. 22]
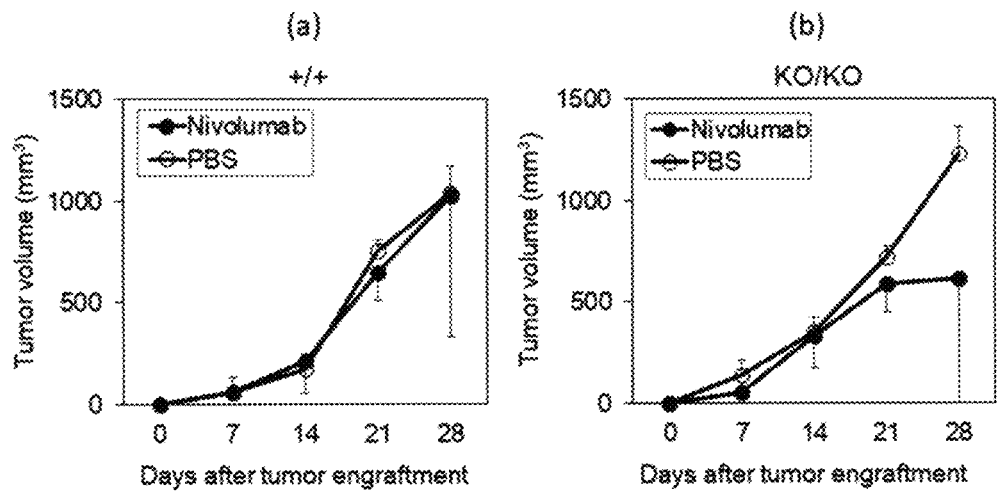
[Fig. 23]
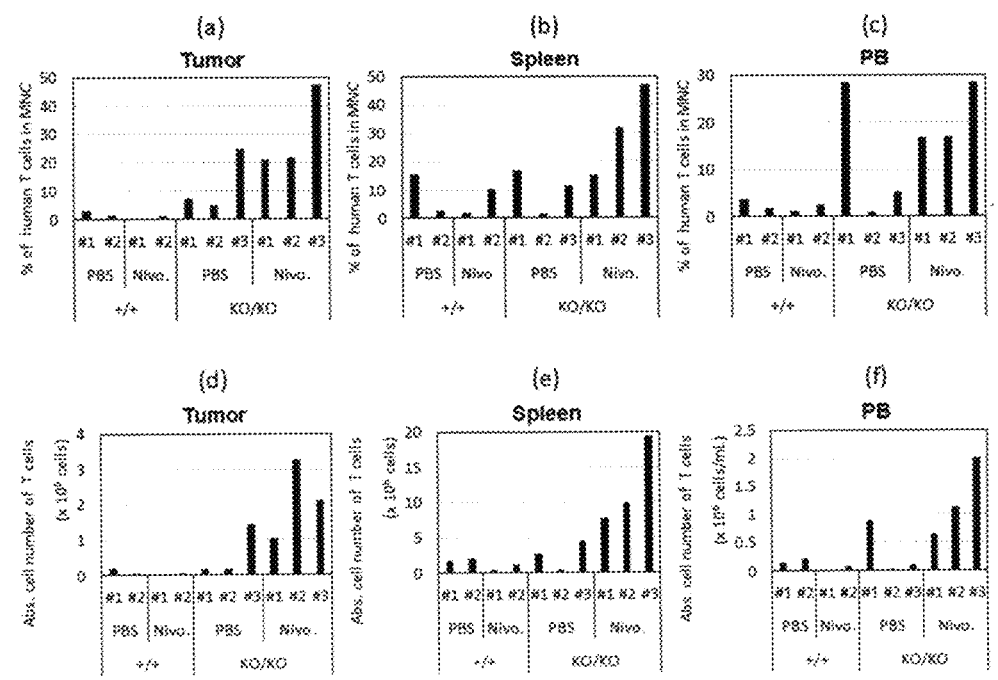

IMMUNODEFICIENT MOUSE

CROSS-REFERENCE TO RELATED APPLICATIONS

This application is a U.S. National Stage Application of International Application PCT/JP2019/037675, filed Sep. 25, 2019, which claims the benefit of the filing date of Japanese Application No. 2018-181930, filed Sep. 27, 2018, and also claims the benefit of the filing date of Japanese Application No. 2018-217229, filed Nov. 20, 2018, the contents of which are all hereby incorporated by reference in their entirety.

TECHNICAL FIELD

The present invention relates to a genetically modified immunodeficient mouse in which a mutation is introduced into the gene of an IL-2 (interleukin-2) receptor γ chain to disrupt the IL-2 receptor γ chain, and in which FcgR (IgG Fc receptor) is functionally not expressed. The present invention further relates to a genetically modified immunodeficient mouse engrafted with human cells in which the human cells are engrafted at a significantly high rate.

BACKGROUND ART

Humanized immunodeficient mice that can be used to analyze human cells and human tissues in vivo are considered experimental animals that are expected to contribute to medicine, not only as research tools for drug discovery, but also as useful tools that can be used to conduct basic studies such as analysis of differentiation or function of human cells in vivo by transplanting human cells into the mice. The generation of more useful humanized immunodeficient mice has been attempted over the years.

For example, NOG mice (also referred to as "NOD.Cg-Prkdc$^{scid}$Il2rg$^{m1Sug}$/ShiJic," "NOD-scid, il2rg$^{null}$" or the like) were produced by Ito et al. (see, e.g., Patent Document 1) by backcrossing an NOD-scid mouse capable of engrafting human cells and having decreased complement activity, macrophage function, natural killer (NK) cell activity or the like, with a mouse with the knocked out IL-2 receptor γ chain gene, a cytokine receptor common domain (IL2RγKO mouse). The NOG mouse lacks both functional T and B cells, loses NK cell activity, has diminished macrophage function and diminished dendritic cell function, and has excellent heterologous cell engraftment property. The NOG mouse is considered as an immunodeficient mouse having very high engraftment property of human cells and tissues.

Meanwhile, in the immune system, an IgG antibody having a variable region and a constant region in its structure binds to a heterologous antigen such as a pathogen in the variable region. FcgR, a receptor that binds to the constant region of an IgG antibody, is present on the surface of many immune cells. An antigen-specific IgG antibody bound to an antigen or the like binds to FcgR via its constant region. As a result, activation of the immune cells is induced and foreign substances such as pathogens are eliminated.

PRIOR ART DOCUMENT

Patent Document

Patent document 1: Japanese Patent No. 3753321

SUMMARY OF THE INVENTION

Object to be Solved by the Invention

It is known that, by transplanting human cancer cells that highly express tumor-associated antigens into the aforementioned NOG mouse and further administering IgG antibodies that recognize tumor-associated antigens thereto, human cancer growth in the NOG mouse is significantly suppressed. The present inventors have confirmed that IgG antibodies are involved in the antibody-dependent cancer suppression response where such tumor-associated antigens are captured and suppress human cancer cells, via mouse FcgR in the NOG mouse. Thus, for example, when performing a functional evaluation experiment on an antibody drug by human antibody administration, there was a difficulty in determining whether the immune response to the antibody was from human immune cells or from mouse immune cells.

An object of the present invention is to provide an immunodeficient mouse capable of eliminating the effects of immune cells from the immunodeficient mouse on human antibodies and having higher engraftment property of human cells than previous.

Means to Solve the Object

The present inventors have found that when a mouse FcgR gene was further deleted from an NOG mouse, the resulting mouse does not exhibit antibody-dependent-cellular-cytotoxicity (ADCC) activity on tumor, and human cells can be engrafted in the mouse at significantly higher rate than in the NOG mouse. The present inventors have further confirmed that by introducing the human IL-15 gene and engrafting human NK cells in the mouse, only human NK cells become effector cells and ADCC activity can be evaluated. Based on these findings, the present invention has been completed.

That is, the present invention is as follows:

[1] A genetically modified immunodeficient mouse in which a mutation is introduced into the gene of the IL-2 receptor γ chain to disrupt the IL-2 receptor γ chain; which has a mutation of a gene involved in rearrangement of antigen receptor genes of T cells and B cells at both allelic loci; and in which FcgR is functionally not expressed.

[2] The genetically modified immunodeficient mouse according to [1], wherein the mutation of a gene involved in rearrangement of antigen receptor genes of T cells and B cells includes a SCID mutation or a RAG mutation.

[3] The genetically modified immunodeficient mouse according to [1] or [2], wherein the genetically modified immunodeficient mouse is a NOG-FcgR KO mouse.

[4] The genetically modified immunodeficient mouse according to any one of [1] to [3], wherein genes for FcgR include Fcer1g and Fcgr2b.

[5] The genetically modified immunodeficient mouse according to any one of [1] to [4], wherein the genetically modified immunodeficient mouse does not exhibit antibody-dependent cellular cytotoxic activity on a tumor.

[6] A tissue derived from the genetically modified immunodeficient mouse according to any one of [1] to [5].

[7] A somatic cell derived from the genetically modified immunodeficient mouse according to any one of [1] to [5].

[8] A germ cell derived from the genetically modified immunodeficient mouse according to any one of [1] to [5].

[9] An immunodeficient mouse engrafted with a human cell, wherein the human cell is engrafted in the genetically modified immunodeficient mouse according to any one of [1] to [5] at a significantly high rate.

[10] An immunodeficient mouse engrafted with the human cell, wherein according to [9], wherein the human cell is a human peripheral blood mononuclear cell.

[11] A tissue engrafted with a human cell derived from the immunodeficient mouse engrafted with a human cell according to [9] or [10].

[12] A human somatic cell derived from the immunodeficient mouse engrafted with a human cell according to [9] or [10].

[13] A germ cell derived from the immunodeficient mouse engrafted with a human cell according to [9] or [10].

[14] A genetically modified immunodeficient mouse (II) produced by crossing the genetically modified immunodeficient mouse according to any one of [1] to [5] with a genetically modified immunodeficient mouse (I) into which the human IL-15 gene is introduced.

[15] The genetically modified immunodeficient mouse (II) according to [14], wherein the genetically modified immunodeficient mouse (I) is an NOG-hIL-15 Tg mouse capable of expanding and retaining a human NK cell.

[16] A tissue derived from the genetically modified immunodeficient mouse (II) according to [14] or [15].

[17] A somatic cell derived from the genetically modified immunodeficient mouse (II) according to [14] or [15].

[18] A germ cell derived from the genetically modified immunodeficient mouse (II) according to [14] or [15].

[19] An immunodeficient mouse engrafted with a human cell (II), wherein the human cell is engrafted in the genetically modified immunodeficient mouse (II) according to [14] or [15] at a significantly high rate.

[20] The immunodeficient mouse engrafted with a human cell (II) according to [19], wherein the human cell is a human peripheral blood mononuclear cell.

[21] A tissue derived from the immunodeficient mouse engrafted with a human cell (II) according to [19] or [20].

[22] A somatic cell derived from the immunodeficient mouse engrafted with a human cell (II) according to [19] or [20].

[23] A germ cell derived from the immunodeficient mouse engrafted with a human cell (II) according to [19] or [20].

[24] A method for evaluating activity or mechanism of action of an antibody against human cell surface protein on a human cell, using the immunodeficient mouse engrafted with a human cell according to claim [9] or [10].

[25] A method for evaluating ADCC activity of a human NK cell, using the genetically modified immunodeficient mouse (II) according to [14] or [15].

[26] A method for evaluating ADCC activity of a human NK cell, using the immunodeficient mouse engrafted with a human cell (II) according to [19] or [20].

[27] An immunodeficient mouse engrafted with a human cell (III), which is used for evaluating a function of an antibody against human cell surface protein by allowing a human immune cell and a human tumor cell to co-exist in a genetically modified immunodeficient mouse.

[28] A method for evaluating a function of an antibody against human cell surface protein against a human cell, using an immunodeficient mouse engrafted with a human cell (III).

[29] A method for evaluating a function of an antibody against human cell surface protein against a human immune cell, using an immunodeficient mouse engrafted with a human cell (III).

Effect of the Invention

According to the present invention, a genetically modified immunodeficient mouse that does not exhibit ADCC activity originated from a mouse cell against tumors and has significantly high engraftment property of human cells can be provided. Furthermore, by transplanting human hematopoietic stem cells into such a mouse to differentiate human immune cells such as T cells, and further transplanting human tumor cells, then administering an antibody against human cell surface protein that acts as an immune checkpoint inhibitor such as an anti-human PD-1 antibody, human tumor immune response of the administered antibody against human cell surface protein can be evaluated. Additionally, by introducing the human IL-15 gene into the genome of the mouse and engrafting human NK cells, the ADCC activity can be evaluated using human NK cells as effector cells.

BRIEF DESCRIPTION OF DRAWINGS

FIG. 1 is a diagram showing the presence or absence of mouse FcgRIII/II (mCD16/32) expression in mouse CD45 (mCD45)$^+$ leukocytes for each mouse. FIGS. 1(b) to 1(d) show the results of (b) NOG mouse, (c) NOG-FcgR KO/+ mouse, and (d) NOG-FcgR KO/KO mouse, respectively. FIG. 1(a) shows the result of a negative control.

FIG. 2 is a diagram showing the frequency of mFcgRIII and mFcgRII-expressing cells in mouse CD45 (mCD45)$^+$ leukocytes.

FIG. 3 is a diagram showing expression of FcgRIII/II (mCD16/32) and the presence or absence of binding of human IgG antibodies in F4/80$^+$CD11b$^+$ monocytes/macrophage fractions in mCD45$^+$ leukocytes after trastuzumab (human IgG antibody) administration. FIGS. 3(a) to 3(c) show the results of (a) negative control, NOG-FcgR KO/+ mouse without trastuzumab administration, (b) human IgG antibody receiving NOG-FcgR KO/+ mouse, and (c) NOG-FcgR KO/KO mouse, respectively.

FIG. 4 is graphs showing measurement results of mouse IgG antibody concentration in plasma after mouse IgG1 monoclonal antibody (mIgG1) administration. FIGS. 4(a) to 4(c) show the results of (a) the case when 100 μg of mouse IgG1 antibody was administered to each of NOG mouse and NOG-FcgR KO/+ mouse, (b) the case when 100 μg of mouse IgG1 antibody was administered to each of NOG-FcgR KO/KO mice, and (c) the case when 20 μg of mouse IgG1 antibody was administered to each of NOG-FcgR KO/KO mice.

FIG. 5 is graphs showing measurement results of concentration of each human IgG antibody in plasma when 100 μg each of three human IgG antibody drugs were administered into NOG-FcgR KO/KO mice, NOG-FcgR KO/+ mice and/or NOG mice intraperitoneally. FIGS. 5(a) to 5(c) show the results of (a) the case when rituximab is administered, (b) the case when trastuzumab is administered, and (c) the case when mogamulizumab is administered to each of the mice.

FIG. 6 is graphs showing measurement results of tumor size after subcutaneous transplantation of Her2-positive gastric cancer cell lines 4-1ST into NOG-FcgR KO/KO mouse and NOG-FcgR KO/+ mouse. FIGS. 6(a) and 6(b) show the results of (a) the case when physiological saline (saline) was administered, and (b) the case when trastuzumab (Herceptin) was administered to each of the mice.

FIG. 7 is graphs showing measurement results of frequency of hCD20$^+$ Daudi cells in blood after transplantation of the human leukemia cell line Daudi into NOG-FcgR KO/KO mouse and NOG-FcgR KO/+ mouse. FIGS. 7(a) and 7(b) show the results of (a) the case when PBS is administered to NOG mouse, NOG-FcgR KO/KO mouse and NOG-FcgR KO/+ mouse, and (b) the case when rituximab is administered to NOG-FcgR KO/KO mouse and NOG-FcgR KO/+ mouse.

FIG. 8 shows (a) a photograph of kidneys and (b) weight measurement results of kidneys of each Daudi-transplanted mouse receiving rituximab or PBS and collected after euthanization on day 23 after Daudi transplantation.

FIG. 9 is graphs showing the frequency of h (human) $CD45^+$ cells in total leukocytes after human hematopoietic stem cell transplantation for NOG-FcgR KO/KO mouse, NOG mouse and NOG-FcgR KO/+ mouse. FIGS. 9(a) and 9(b) show the results of each mouse in (a) males and (b) females.

FIG. 10 is graphs showing details of $hCD45^+$ cells for human hematopoietic stem cell-transplanted NOG-FcgR KO/KO mouse, NOG mouse, and NOG-FcgR KO/+ mouse. FIGS. 10(a) to 10(f) show the results of (a) male $hCD33^+$ myeloid cells, (b) male $hCD19^+$ B cells, (c) male $hCD3^+$ T cells, (d) female $hCD33^+$ myeloid cells, (e) female $hCD19^+$ B cells, and (f) female $hCD3^+$ T cells.

FIG. 11 is graphs of engraftment ratio of $hCD45^+$ cells and the engrafted cell number in hematopoietic organs (bone marrow, spleen, blood) measured for collected after euthanization, human hematopoietic stem cell-transplanted NOG-FcgR KO/KO mouse, NOG mouse, and NOG-FcgR KO/+ mouse. FIGS. 11(a) to 11(f) show (a) the engraftment ratio in bone marrow, (b) the engraftment ratio in spleen, (c) the engraftment ratio in blood, (d) the engrafted cell number in bone marrow, (e) the engrafted cell number in spleen, and (f) the engrafted cell number in blood.

FIG. 12 is graphs of the frequency and the number of engrafted $hCD3^+$ T cells, $hCD19^+$ B cells, $hCD33^+$ myeloid cells, and $hCD56^+$ NK cells in hematopoietic organs (bone marrow, spleen, blood) measured in collected after euthanization, human hematopoietic stem cell-transplanted NOG-FcgR KO/KO mouse, NOG mouse, and NOG-FcgR KO/+ mouse.

FIGS. 12(a) to 12(f) show (a) the engraftment ratio of each cell in bone marrow, (b) the engraftment ratio of each cell in spleen, (c) the engraftment ratio of each cell in blood, (d) the cell number of each cell in bone marrow, (e) the cell number of each cell in spleen, and (f) the cell number of each cell in blood.

FIG. 13 is graphs evaluating the status of differentiation of T cell subpopulations for human hematopoietic stem cell-transplanted NOG-FcgR KO/KO mouse, NOG mouse, and NOG-FcgR KO/+ mouse. FIGS. 13(a) and 13(b) show (a) results in spleen and blood for subpopulations of $CD4^+$ T cells, $CD8^+$ T cells, $CD4^+CD8^+$ DP T cells, and (b) results for hPD-1.

FIG. 14 is graphs of the increase or decrease in human immune cells including human T cells, in each hematopoietic tissue of bone marrow, spleen, and blood analyzed by flow cytometry for human hematopoietic stem cell-transplanted NOG-FcgR KO/KO mouse, NOG mouse, and NOG-FcgR KO/+ mouse collected after euthanization after administration of anti-human PD-1 antibody. FIGS. 14(a) to 14(f) show (a) engraftment ratio of $hCD45^+$ cells in bone marrow, (b) engraftment ratio of $hCD45^+$ cells in spleen, (c) engraftment ratio of $hCD45^+$ cells in blood, (d) $hCD45^+$ cell number in bone marrow, (e) $hCD45^+$ cell number in spleen, and (f) $hCD45^+$ cell number in blood.

FIG. 15 is graphs of the frequency and engrafted cell numbers of $hCD3^+$ T cells, $hCD19^+$ B cells, $hCD33^+$ myeloid cells, and $hCD56^+$ NK cells in hematopoietic organs (bone marrow, spleen, blood) for human hematopoietic stem cell-transplanted NOG-FcgR KO/KO mouse, NOG mouse and NOG-FcgR KO/+ mouse collected after euthanization after anti-human PD-1 antibody administration. FIGS. 15(a) to 15(f) show (a) the engraftment ratio of each cell population in bone marrow, (b) the engraftment ratio of each cell population in spleen, (c) the engraftment ratio of each cell population in blood, (d) the cell number of each cell population in bone marrow, (e) the cell number of each cell population in spleen, and (f) the cell number of each cell population in blood.

FIG. 16 is graphs of further examination of the subpopulations of T cells for $hCD3^+$ T cells in spleen for human hematopoietic stem cell-transplanted NOG-FcgR KO/KO mouse, NOG mouse and NOG-FcgR KO/+ mouse, collected after euthanization after anti-human PD-1 antibody administration. FIGS. 16(a) and 16(b) show (a) the engraftment ratio in spleen for the subpopulations of $CD4^+$ T cells, $CD8^+$ T cells, $CD4^+CD8^+$ DP T cells, and (b) the cell numbers in spleen for the subpopulations of $CD4^+$ T cells, $CD8^+$ T cells, $CD4^+CD8^+$ DP T cells.

FIG. 17 is graphs showing (a) the engraftment ratio of $hCD45^+$ cells when 2,500,000 cells were transplanted, (b) the engrafted cell number of $hCD45^+$ cells when 2,500,000 cells were transplanted, (c) the engraftment ratio of $hCD45^+$ cells when 1,500,000 cells were transplanted, and (d) the engrafted cell number of $hCD45^+$ cells when 1,500,000 cells were transplanted, for human peripheral blood mononuclear cell (PBMC)-transplanted NOG-FcgR KO/KO mouse and NOG mouse.

FIG. 18 shows (a) the frequency and engraftment ratio of $hCD3^+$ T cells, $hCD19^+$ B cells in $hCD45^+$ cells when 2,500,000 cells were transplanted, (b) the engraftment ratio for the subpopulations of $CD4^+$ T cells, $CD8^+$ T cells, $CD4^+CD8^+$ DP T cells when 2,500,000 cells were transplanted, (c) the frequency and engraftment ratio of $hCD3^+$ T cells, $hCD19^+$ B cells in $hCD45^+$ cells when 1,500,000 cells were transplanted, (d) the engraftment ratio for the subpopulations of $CD4^+$ T cells, $CD8^+$ T cells, $CD4^+CD8^+$ DP T cells when 1,500,000 cells were transplanted, for collected after euthanization, human PBMC-transplanted NOG-FcgR KO/KO mouse and NOG mouse.

FIG. 19(a) shows the analysis results by flow cytometry of $hCD3^+$ T cells from human PBMC-transplanted NOG mouse, NOG-FcgR KO/+ mouse, and NOG-FcgR KO/KO mouse. FIG. 19(b) is graphs showing the presence or absence of induction of ADCC activity on human PD-$1^+$ T cells when an anti-human PD-1 antibody was administered after PBMC transplantation.

FIG. 20 is graphs showing (a) the engraftment property of $hCD45^+$ cells and (b) the frequency of NK cells, for a mouse crossed with NOG-hIL-15 Tg mouse.

FIG. 21 shows the measurement results of kidney weight of each of rituximab or PBS-administered, Daudi-transplanted hIL-15 Tg mouse collected after euthanization after Daudi transplantation.

FIG. 22 is graphs showing the results of (a) the experiment when administering PBS or nivolumab to HSC-4 transplanted NOG (-FcgR+/+) mouse, and (b) the experiment when administering PBS or nivolumab to HSC-4 transplanted NOG-FcgR KO/KO mouse.

FIG. 23 is graphs showing the frequency (a, b, c) and the number (d, e, f) of $hCD45^+CD3^+$ T cells in hematopoietic organs (spleen and blood) and in tumors of NOG-FcgR KO/KO mouse and NOG (-FcgR+/+) mouse collected after euthanization after 4 weeks of HSC-4 transplantation. FIGS. 23(a) to 23(f) show (a) the frequency of $hCD3^+$ T cells in tumor, (b) the frequency of $hCD3^+$ T cells in spleen, (c) the frequency of hCD3+ T cells in blood, (d) the number of engrafted hCD3+ T cells in tumor, (e) the number of engrafted hCD3+ T cells in spleen, and (f) the number of engrafted hCD3+ T cells in blood.

MODE OF CARRYING OUT THE INVENTION

The genetically modified immunodeficient mouse of the present invention is not particularly limited if it is a mouse which has a mutation introduced into the IL-2 receptor γ chain gene to be deficient in the IL-2 receptor γ chain, and in which FcgR is functionally not expressed. The genetically modified immunodeficient mouse refers to a mouse in which the immune action performed by a wild-type gene does not function due to a genetic modification in which a gene mutation such as substitution of one or more bases with another base, deletion of one or more bases, insertion of one or more bases, an out-of-frame that deviates from a reading frame of an amino acid, and/or a combination of these is introduced for the DNA sequence of a wild-type gene encoding a protein that directs a particular immune function. The wild-type described above is the most common allele or polymorphism seen in a population, and examples thereof can include a mouse that has not been genetically modified by mutation or artificially manipulation.

The present invention further includes a genetically modified immunodeficient mouse (II) produced by crossing the genetically modified immunodeficient mouse described above with a genetically modified immunodeficient mouse (I) in which the human IL-15 gene was introduced into the genetically modified immunodeficient mouse.

The mouse according to the present invention can include a mammal belonging to the genus Mus, family Muridae, Rodentia.

The mouse which has a mutation introduced into the IL-2 receptor γ chain gene to be deficient in the IL-2 receptor γ chain according to the present invention can include a mouse in which the IL-2 receptor γ chain is functionally not expressed.

It is known in human and mouse that the aforementioned IL-2 receptor consists of three types of proteins called alpha (α), beta (β) and gamma (γ) chains. While the aforementioned IL-2 receptor γ chain alone does not have binding ability to IL-2, a heterodimer composed of the β- and γ-chains is an intermediate-affinity receptor for IL-2, and a heterotrimer composed of the α-, β- and γ-chains is a high-affinity receptor for IL-2.

The IL-2 is a cytokine, and the action of IL-2 can include transmitting IL-2 signals from the cytoplasm into the nucleus by binding to an IL-2 receptor present on the cell surface, inducing proliferation of T and B cells and activation of NK cells, and the like. The case in which the IL-2 receptor γ chain is not functionally expressed can thus include the case in which the IL-2 receptor has lost its binding ability to IL-2 due to a mutation introduced into an IL-2 receptor γ chain gene, or the case in which signaling does not occur.

The genetically modified immunodeficient mouse in which FcgR is functionally not expressed can include a mouse in which FcgR does not function as a receptor protein due to a mutation in the gene encoding FcR. The functions of FcgR as a receptor protein can include transmitting signals into cells by specifically binding to a complex of antigen bound to an IgG antibody. In the mouse of the present invention, it is essential that such mutations are located at both allelic loci.

The FcgR is a receptor protein normally present on the surface of immune system cells such as T cells, B cells, NK cells, macrophages, and dendritic cells. The FcgR is broadly classified, based on gene structure similarity, into three types: FcgRI encoded by the FcgrI gene (CD64 antigen), FcgRII encoded by the FcgrII gene (CD32 antigen), and FcgRIII encoded by the FcgrIII gene (CD16 antigen). It should be noted that the common γ chain in FcR (also referred to as FcRg or FceRIg) provides a common constitutive factor for FcgRI and FcgRIII.

In the mouse of the present invention, it is further essential that mutations in the genes involved in the rearrangement of the antigen receptor genes of T and B cells are located at both allelic loci. Examples of such mutations can include a SCID mutation or a RAG mutation. The SCID mutation is a mutation of a DNA dependent protein kinase (Protein kinase, DNA activated, catalytic polypeptide: Prkdc) gene found in mice exhibiting Severe Combined Immuno-Deficiency (SCID).

The RAG mutation can include a mutation in Recombination activating gene (Rag)-1 or Rag-2 gene. Such two genes are genes expressed in immature lymphocytes, which have essential effects on the rearrangement of immunoglobulin genes and T cell receptors and are essential for the maturation of T and B cells.

The mouse that has mutations in the gene involved in the rearrangement of the antigen receptor genes of T and B cells, including the SCID mutation and/or RAG mutation, at both allelic loci are unable to genetically rearrange T and B cells due to DNA repair abnormality, so that T and B cells fail to reach the maturation stage and the functions of T and B cells are lost. In the mouse of the present invention, such mutations must be at both allelic loci.

The method for producing the genetically modified immunodeficient mouse of the present invention which has a mutation introduced into the IL-2 receptor γ chain gene to be deficient in the IL-2 receptor γ chain and in which FcgR is not functionally expressed can include a method of introducing the mutation into the IL-2 receptor γ chain gene and the mutation in the FcgR gene into a mouse by a conventionally known genome editing method, a method of generating such mouse by crossing conventionally known mice, and a method of generating such a mouse with a combination of a method to introduce a mutation into a mouse by a known genome editing method and a method by crossing.

Examples of the known genome editing methods include a TALEN system using a transcriptional activation-like effector nuclease, a Zn finger nuclease system, and a CRISPR/Cas9 (clustered regularly interspaced short palindromic repeats/CRISPR associated proteins) system. The CRISPR/Cas9 described above can be used as a preferred genetic modification technique in that a mutation introduced into the IL-2 receptor γ chain gene or a mutation in the FcgR gene can be introduced into a mouse ES cell or mouse iPS cell by editing the genome by cleaving the DNA duplex (Double Strand Breaks) and deleting, replacing, or inserting anywhere in the genomic sequence.

The method of generating a genetically modified immunodeficient mouse by crossing using conventionally known mice described above are not particularly limited if it is a method of generating a genetically modified immunodeficient mouse which has a mutation introduced into an IL-2 receptor γ chain gene to be deficient in the IL-2 receptor γ chain, and in which FcgR (IgG Fc receptor) is functionally not expressed. Examples of such methods include a method of crossing a mouse in which a mutation is introduced into the IL-2 receptor γ chain gene to be deficient in the IL-2 receptor γ chain with a mouse which has no functional expression of FcgR (FcgR KO mouse). It should be noted that "FcgR KO mouse" herein means a mouse that does not express FcgR function due to deficiency of function caused by mutations at both allelic loci (KO/KO) relative to the wild-type (+/+), and the FcgR KO mouse does not include heterotype (KO/+).

Specific examples of the mouse in which a mutation is introduced into the IL-2 receptor γ chain to be deficient in the IL-2 receptor γ chain include known mice such as NOG mouse, C57BL/6-IL2rg$^{null}$ mouse, C57BL/6-Rag2$^{null}$IL2rg$^{null}$ mouse, NOD/Shi-Rag2$^{null}$IL2rg$^{null}$ mouse, BALB/c-Rag2null-IL2rg$^{null}$ mouse, and BALB/c-IL2rg$^{null}$ mouse, and NOG mouse, C57BL/6-Rag2$^{null}$IL2rg$^{null}$ mouse, NOD/Shi-Rag2$^{null}$IL2rg$^{null}$ mouse, BALB/c-Rag2null-IL2rg$^{null}$ mouse are preferable in terms of further having a SCID mutation or a RAG mutation at both allelic loci, and NOG mouse, in which T and B cell functions are deleted, NK cell activity is diminished, macrophage function is diminished, and dendritic cell function is diminished, is particularly preferable.

Specific examples of the above FcgR gene include an FcerI gene, an FcgrI gene, an FcgrII gene, and an FcgrIII gene. Specific examples of the FcgR KO mouse described above include an NOD-Fcer1g$^{null/null}$ mouse that is deficient in the FcerI gene, an NOD-Fcgr2b$^{null/null}$ mouse that is deficient in the FcgrII gene, an NODIII−/− mouse that is deficient in the FcgrIII gene, an NOD-Fcer1g$^{null/null}$Fcgr2b$^{null/null}$ mouse that is deficient in the FcerI gene and the FcgrII gene, and preferred examples include an NOD-Fcer1g$^{null/null}$Fcgr2b$^{null/null}$ mouse which has no functional expression of FcgR including Fcer1g and Fcgr2b.

Hereinafter, the production method by crossing a genetically modified immunodeficient mouse which has a mutation introduced into the IL-2 receptor γ chain gene to be deficient in the IL-2 receptor γ chain and in which FcgR is functionally not expressed, is described below using a method in which, for example, an NOG mouse is used as a mouse deficient in the IL-2 receptor γ chain, and an NOD-Fcer1g$^{null/null}$Fcgr2b$^{null/null}$ mouse in which the non-functioned FcgR gene is Fcer1g and Fcgr2b is used as a mouse in which FcgR is functionally not expressed (FcgR KO/KO mice (genotype), FcgR KO mice (phenotype)), as an example. It should be noted that because IL-2rg is present on chromosome X, when the genotype of male mouse is il2rg$^{null/Y}$ and the genotype of female mouse is il2rg$^{null/null}$, the produced mouse is a mouse in which IL-2rg is deficient at both allelic loci.

The aforementioned NOG mouse is a mouse produced by backcrossing a NOD-scid mouse, a combination mouse of a mouse named as Non Obese Diabetes (NOD) mouse because of its similarity to the pathophysiology of human type 1 diabetes (insulin-dependent diabetes) (see, for example, Jikken Dobutsu. 29: 1-13, 1980) and a SCID mouse that exhibits severe immune failure due to a mutation in a DNA-dependent protein kinase (Prkdc) gene resulting in loss of T and B cell functions, with a mouse (IL-2RγKO mouse) with knocked out gene for the IL-2 receptor γ-chain, a common domain of several cytokine receptors, whose gene is a gene responsible for X-linked severe combined immunodeficiency (XSCID) (Ohbo K et al., Blood 1996) in accordance with the Cross Intercross method (Inbred Strains in Biomedical Research, M. F. W. Festing, 1979, The Macmillan Press, London and Basingstoke). Specifically, NOD mouse can be produced with reference to JP Patent No. 3753321 and is available from the Central Institute for Experimental Animals, a Public Interest Incorporated Foundation.

The aforementioned NOD-Fcer1g$^{null/null}$Fcgr2b$^{null/null}$ mouse is a mouse produced by Toshiyuki Takai, Tohoku University. The mouse is stored at RIKEN BioResource Research Center (RIKEN BRC), a National Research and Development Corporation, and is available as a frozen embryo or an individually restored mouse.

Examples of the method for generating a genetically modified immunodeficient mouse of the present invention when using an NOG mouse and a NOD-Fcer1g$^{null/null}$Fcgr2b$^{null/null}$ mouse include a method comprising the following steps a) to f) sequentially:
  a) crossing a male NOD-Fcer1g$^{null/null}$Fcgr2b$^{null/null}$ mouse with a female NOG mouse;
  b) selecting a female NOD-scid/+, il2rg$^{null/+}$-Fcer1g$^{null/+}$Fcgr2b$^{null/+}$ mouse;
  c) backcrossing the mouse selected in b) with a male NOG mouse;
  d) selecting a male NOD-scid, il2rg$^{null/Y}$-Fcer1g$^{null/+}$Fcgr2b$^{null/+}$ mouse and a female NOD-scid, il2rg$^{null/null}$-Fcer1g$^{null/+}$Fcgr2b$^{null/+}$ mouse;
  e) sibling crossing the male mouse and the female mouse selected in d); and
  f) selecting 1) a male NOD-scid, il2rg$^{null/Y}$-Fcer1g$^{null/null}$, Fcgr2b$^{null/null}$ and 2) a female NOD-scid, il2rg$^{null/null}$-Fcer1g$^{null/null}$, Fcgr2b$^{null/null}$ as a "NOG-FcgR KO/KO mouse."

Each genotype of the mouse in the production step described above can be confirmed by routine methods using a PCR method with appropriate primers.

The present invention also relates to a tissue, a somatic cell and a germ cell derived from the genetically modified immunodeficient mouse described above.

Examples of the tissue derived from the genetically modified immunodeficient mouse include liver, spleen, brain, kidney, lung, skin, bladder, stomach, gallbladder, pancreas, adrenal gland, prostate, large intestine, small intestine, esophagus, muscle, mammary grand, thymus, lymph node, nerve, trachea, eyeball, bone, heart, fat, genital organ (e.g., ovary, uterus, testis, seminal vesicle), embryo, and thyroid, and preferably, spleen, bone marrow, and liver.

Examples of the somatic cell derived from the genetically modified immunodeficient mouse include a tissue stem cell such as a mesenchymal stem cell, a hematopoietic stem cell, an adipose tissue-derived stromal cell, an adipose tissue-derived stromal stem cell, a neural stem cell and a sperm stem cell, a tissue progenitor cell, a muscle cell, a fibroblast, an epithelial cell, a lymphocyte, a leukocyte, a T cell, a B cell, and a myeloid cell.

Examples of the germ cell derived from the genetically modified immunodeficient mouse include a sperm and an egg of the mouse.

Advantageous characteristics of the mouse of the present invention can include that, in the mouse, mouse phagocytic cells acting via mouse FcgR do not exhibit ADCC activity on a solid tumor or leukemia cells (collectively also referred to as "tumor") bound to a cancer antigen-specific human antibody, and human cells are engrafted in the mouse at significantly higher rate than in conventionally known mice.

The method for examining whether the mouse of the present invention exhibits ADCC activity described above or not can include a method of transplanting a human solid cancer cell line into each of the mouse of the present invention and a mouse for comparison by subcutaneous transplantation or the like, administering a human antibody to each of the mice, to measure a tumor size with the human solid cancer cell line described above in a timely manner. For example, when the size (volume) of the tumor mass in the mouse of the present invention about 20 days after administration of the human antibody is three times greater, preferably four times greater, more preferably five or more times greater than the size of the tumor in a mouse for comparison expressing mouse FcgR, it can be determined that the mouse of the present invention does not exhibit ADCC activity on the tumor.

Other methods of examining whether the mouse of the present invention exhibits the ADCC activity or not can include a method of transplanting a human leukemia cell line into each of the mouse of the present invention and a mouse for comparison in blood, and administering a human antibody to each of the mice, to confirm the status of proliferation of human leukemia cells in the blood in a timely manner. Examples of such cases can include a case in which the frequency of human leukemia cells in the total leukocytes of the mouse of the present invention about 20 days after administration of the human antibody is three times greater, preferably four times greater, more preferably five times greater, and even more preferably eight or more times greater than the frequency of human leukemia cells in the total leukocytes of a mouse FcgR-expressed mouse for comparison. In such cases, it can be determined that the mouse of the present invention does not exhibit the ADCC activity on the human leukemia cells.

Yet another method of examining whether the mouse of the present invention exhibits the ADCC activity or not can include a method of measuring the weight of the tissue localized by cancer cells on day 23 after transplantation for the mouse into which a human leukemia cell line is transplanted in blood and a human antibody is administered; comparing the measured weight of the tissue with a weight of the tissue of a mouse for comparison expressing mouse FcgR; and determining, when the weight of the tissue of the mouse of the present invention is significantly heavier, the mouse of the present invention does not exhibit ADCC activity. Examples of such cases can include a case in which the weight of the kidney, one of the tissues in which the cancer cells are localized, in the mouse of the present invention about 20 days after administration of the human antibody is 1.5 times greater, preferably 1.7 times greater, more preferably 2 times greater than the weight of the kidney in the mouse for comparison. In such cases, it can be determined that the mouse of the present invention does not exhibit the ADCC activity on the human leukemia cells.

The mouse of the present invention can include an immunodeficient mouse engrafted with a human cell in which a human cell is engrafted at a significantly high rate in the genetically modified immunodeficient mouse which has a mutation introduced into the IL-2 receptor γ chain gene to be deficient in the IL-2 receptor γ chain and has no functional expression of FcgR. The method for producing such a mouse can include a method of transplanting human cells after irradiating the genetically modified immunodeficient mouse of the present invention with irradiation such as X-rays which destroys the bone marrow environment to improve the engraftment capacity of human cells. Preferable examples of the intensity of the irradiation can include from 0.5 to 2.0 Gy. Preferable time period of transplantation is within 24 hours after irradiation. In present invention, examples of the human cells that can be transplanted into the mouse of the present invention can include a human hematopoietic stem cell, a human peripheral blood mononuclear cell, and a human NK cell.

The method of evaluating the engraftment property of a human cell transplanted into the genetically modified immunodeficient mouse described above can include a method of identifying human cells in the mouse by the presence of a cell surface marker having a specific epitope site to which the antibody binds. For example, the engraftment of a human leukocyte (hCD45$^+$ cell) in total leukocytes of peripheral blood can be determined when the presence of hCD45$^+$ cell is confirmed present by flow cytometry analysis with an anti-hCD45 antibody. This is because, when a human hematopoietic stem cell (hCD34$^+$ cell), a source of human blood cells, is engrafted in a genetically modified immunodeficient mouse, human blood cells including leukocytes, erythrocytes and platelets are differentiated and expanded from the engrafted human hematopoietic stem cells, and the leukocyte, an immune cell, is stored in blood and each immune tissue of the mouse.

Examples of the case where the engraftment of human cells (tissues) is significantly high in the mouse of the present invention can include a case in which the engraftment property of human tissues is significantly high compared to that in NOG mouse in the analysis of Two-way ANOVA ($p<0.05$) at week 16 after transplantation. The fact that the engraftment of human tissues in the mouse of the present invention is significantly higher than that in NOG mouse is an effect that even a person skilled in the art would not have expected, since there is a knowledge that, for example, in an NOD-Fcer1g$^{null/null}$ Fcgr2b$^{null/null}$ mouse, the human tissue engraftment is almost not observed.

When the human cell is a human hematopoietic stem cell, the method of transplanting a human hematopoietic stem cell can include a method of transplanting 1,000 to 250,000, preferably 10,000 to 100,000, more preferably 25,000 to 75,000 hCD34$^+$ hematopoietic stem cells into an adult mouse from the tail vein within one day after X-ray irradiation.

The characteristic of the immunodeficient mouse engrafted with a human cell in which a human hematopoietic stem cell is engrafted can include a significantly large number of hCD19$^+$ cells that is indicative of differentiation into B cells can be detected in the spleen. Examples of the significantly large number can include 1.5 times greater, preferably 2 times greater, more preferably 2.5 or more times greater than that in NOG mice. Whether the hCD19$^+$ cells described above are present or not can be confirmed, for example, by flow cytometry analysis using an anti-hCD19 antibody.

The characteristic of the spleen of the mouse engrafted with the human hematopoietic stem cells can include normal differentiation from hCD3$^+$ T cells further into subpopulations of hCD4$^+$ T cells, hCD8$^+$ T cells or hCD4$^+$CD8$^+$ double positive (DP) T cells and reconstitution of a blood immune system. In the differentiated hCD4$^+$ T cells, hCD8$^+$ T cells and hCD4$^+$CD8$^+$ double positive (DP) T cells, a programmed cell death 1 (PD-1) protein molecule (hPD-1) expressed in human T cells is expressed. Whether the aforementioned hCD3$^+$ T cells, hCD4$^+$ T cells, hCD8$^+$ T cells, hCD4$^+$CD8$^+$ double positive T cells, hCD19$^+$ cells, PD-1$^+$ cells are present or not can be confirmed, for example, by flow cytometry analysis using a series of antibodies.

When the human cell is a human peripheral blood mononuclear cell, examples of the method of transplanting a human peripheral blood mononuclear cell can include a method of transplanting 100,000 to $1\times10^7$ human peripheral blood mononuclear cells, preferably 500,000 to 5,000,000, preferably 1,000,000 to 3,000,000, more preferably 1,250, 000 to 2,750,000, even more preferably 1,300,000 to 2,500,000, particularly preferably 1,450,000 to 1,750,000 human peripheral blood mononuclear cells from the tail vein.

Examples of the mouse in which a human peripheral blood mononuclear cell is engrafted can include an immunodeficient mouse engrafted with a human cell having significantly high rate of engrafted human cell in which the number of engrafted cells of hCD45 positive leukocytes (hCD45$^+$ cells) is 2 times greater, preferably 3 times greater, more preferably 5 times greater, even more preferably 10 times greater than the number of engrafted cells in NOG mouse at week 6 after human peripheral blood mononuclear cell transplantation; the frequency of hCD45$^+$ cells in human peripheral blood mononuclear cells at week 6 after human peripheral blood mononuclear cell transplantation is 1% or more, preferably 2% or more, more preferably 4% or more, further preferably 5% or more, particularly preferably 6% or more; and/or 80% or more, preferably 90% or more, more preferably 95% or more, still preferably 97% or more of hCD45$^+$ cells are comprised of hCD3$^+$ T cells.

As above, by evaluating the engraftment of human cells transplanted into the genetically modified immunodeficient mouse, the immunodeficient mouse engrafted with a human cell can be used to evaluate the activity and mechanism of action of an antibody against human cell surface protein on human cells.

The present invention also relates to a tissue, a somatic cell and a germ cell derived from the aforementioned immunodeficient mouse engrafted with a human cell. Evaluation of the activity and mechanism of action of an antibody against human cell surface protein on the human cells described above can also be performed using the tissue, the somatic cell or the germ cell derived from the aforementioned immunodeficient mouse engrafted with a human cell.

Examples of the tissue derived from the immunodeficient mouse engrafted with a human cell can include liver, spleen, brain, kidney, lung, skin, bladder, stomach, gallbladder, pancreas, adrenal gland, prostate, large intestine, small intestine, esophagus, muscle, mammary gland, thymus, lymph node, nerve, trachea, eyeball, bone, heart, fat, genital organ (e.g., ovary, uterus, testis, seminal vesicle), embryo, and thyroid, and preferably, spleen, bone marrow, and liver.

Examples of the somatic cell derived from the immunodeficient mouse engrafted with a human cell can include a tissue stem cell such as a mesenchymal stem cell, a hematopoietic stem cell, an adipose tissue-derived stromal cell, an adipose tissue-derived stromal stem cell, a neural stem cell and a sperm stem cell, a tissue progenitor cell, a muscle cell, a fibroblast, an epithelial cell, a lymphocyte, a leukocyte, a T cell, a B cell, and a myeloid cell.

Examples of the germ cell derived from the immunodeficient mouse engrafted with a human cell can include a sperm and an egg of the mouse.

The genetically modified immunodeficient mouse (II) is not particularly limited if it is a genetically modified immunodeficient mouse (II) produced by crossing the genetically modified immunodeficient mouse of the present invention with a genetically modified immunodeficient mouse (I) into which the human IL-15 gene has been introduced. Specific examples of the genetically modified immunodeficient mouse (I) into which the human IL-15 gene has been introduced can include an NOG-hIL-15 Tg mouse, an NOG mouse into which the human IL-15 gene has been introduced (also referred to as "NOD-scid, IL-2rγ$^{null}$-hIL-15 Tg mouse") (see, e.g., Japanese unexamined Patent Application Publication No. 2016-220559). Examples of the immunodeficient mouse engrafted with a human cell (II) can include a genetically modified immunodeficient mouse engrafted with human cells (II) such as human peripheral blood mononuclear cells and human NK cells. Such genetically modified immunodeficient mouse (II) and immunodeficient mouse engrafted with human cells (II) can also be included in the mouse of the present invention.

In the immunodeficient mouse engrafted with a human cell (II) in which the human NK cell is transplanted in the genetically modified immunodeficient mouse (II) described above, it is desirable that hCD56$^+$ cells are detected at 60% or more, preferably 70% or more, more preferably 80% or more of the engrafted hCD45$^+$ cells. Preferred examples of the genetically modified immunodeficient mouse (II) include the NOG-FcgR KO/KO hIL-15 Tg mouse. The presence or absence of the hCD56$^+$ cells described above can be confirmed, for example, by flow cytometry analysis using an anti-hCD56 antibody.

In the genetically modified immunodeficient mouse (II) and immunodeficient mouse engrafted with a human cell (II) above, only human NK cells become effector cells without being affected by mouse phagocytes, thus ADCC activity can be evaluated.

That is, in the genetically modified immunodeficient mouse (II) and immunodeficient mouse engrafted with a human cell (II), where the human NK cells have become effector cells, mouse phagocytes acting via mouse FcgR do not exhibit ADCC activity on tumors bound to cancer antigen-specific human antibodies. Thus, screening for candidate agents for antibody drugs against tumors can be performed using the genetically modified immunodeficient mouse (II) or immunodeficient mouse engrafted with a human cell (II).

For example, by transplanting a human cancer cell into a genetically modified immunodeficient mouse (II), then administering a human NK cell and a cancer antigen-specific human antibody as a candidate agent for antibody drugs, ADCC activity on human cancer cells where only human NK cells are effector cells can be evaluated. Specifically, when transplanting a human cancer cell, and then administering a human NK cell and the candidate agent into a genetically modified immunodeficient mouse (II) result in a suppression of the weight increase of a tissue in which the cancer cells are localized, it can be determined that the candidate agent has a suppression effect on cancer cells. With similar criteria, ADCC activity on human cancer cells where only human NK cells are effector cells can be evaluated by transplanting a human cancer cell and then administering a cancer antigen-specific human antibody as the candidate agent for antibody drugs into the immunodeficient mouse engrafted with a human cells (II) in which NK cell is engrafted, and the screening for the candidate agent described above can be performed.

The present invention also relates to a tissue, a somatic cell, and a germ cell derived from the genetically modified immunodeficient mouse (II) or immunodeficient mouse engrafted with a human cell (II) described above. The screening for the candidate agents described above can also be performed using the tissue, the somatic cell or the germ cell.

Examples of the tissue derived from the genetically modified immunodeficient mouse (II) or immunodeficient mouse engrafted with a human cell (II) can include liver, spleen, brain, kidney, lung, skin, bladder, stomach, gallbladder, pancreas, adrenal gland, prostate, large intestine, small intestine, esophagus, muscle, mammary gland, thymus, lymph node, nerve, trachea, eyeball, bone, heart, fat, genital organ (e.g., ovary, uterus, testis, seminal vesicle), embryo, and thyroid, and preferably, spleen, bone marrow, and liver.

Examples of the somatic cells derived from the genetically modified immunodeficient mouse (II) or immunodeficient mouse engrafted with a human cell (II) can include a tissue stem cell such as a mesenchymal stem cell, a hematopoietic stem cell, an adipose tissue-derived stromal cell, an adipose tissue-derived stromal stem cell, a neural stem cell and a sperm stem cell; a tissue progenitor cell, a muscle cell, a fibroblast, an epithelial cell, a lymphocyte, a blood cell, a differentiated NK cell from these cells, a T cell, a B cell, and a myeloid cell.

Examples of the germ cells derived from the genetically modified immunodeficient mouse (II) or immunodeficient mouse engrafted with a human cell (II) can include a sperm and an egg.

Hereinafter the present invention will be described in more detail by way of Examples, but the technical scope of the present invention is not limited to these illustrations.

EXAMPLES

Example 1

Production of NOG-FcgR KO/KO Mouse

NOG mice were obtained from the Central Institute for Experimental Animals. Cryopreservation embryos (RBRC02330) of NOD-Fcer1g$^{null/null}$Fcgr2b$^{null/null}$ mice (NOD-FcgR KO/KO mice) were obtained via RIKEN BRC.
Procedure for Production of NOG-FcgR KO/KO Mouse
From the NOG mouse and the NOD-Fcer1g$^{null/null}$Fcgr2b$^{null}$ mouse, NOG-FcgR KO/KO mouse was produced by the following steps.
(1) (Generation 0 (F=0) to Generation 1 (F=1)
A male NOD-FcgR KO/KO mouse restored from the cryopreserved embryo was crossed with a female NOG mouse to yield four female NOD-scid/+, il2rg$^{null}$/+-Fcer1g$^{null/+}$Fcgr2b$^{null/+}$ mice (F=1).
(2) (Generation 1 to Generation 2)
Each of these 4 female mice were backcrossed with an NOG mouse to yield 2 male NOD-scid, il2rg$^{null/Y}$-Fcer1g$^{null/+}$Fcgr2b$^{null/+}$ mice and 2 female NOD-scid, il2rg$^{null/null}$-Fcer1g$^{null/+}$Fcgr2b$^{null/+}$ mice (hereinafter collectively referred to as "NOG-FcgR KO/+ mice (genotype)").
(3) (Generation 2 to Generation 3)
The NOG-FcgR KO/+ mice were sibling crossed each other, and male NOD-scid, il2rg$^{null/Y}$-Fcer1g$^{null/null}$, Fcgr2b$^{null/null}$ and female NOD-scid, il2rg$^{null/null}$-Fcer1g$^{null/null}$, Fcgr2b$^{null/null}$ were selected to yield "NOG-FcgR KO/KO mice (genotype), NOG-FcgR KO mice (phenotype)".

In each of the above steps, mouse genetic test was conducted by adding 100 μg/mL protein kinase K-containing Lysis buffer to the tissue pieces of a mouse and dissolving them at 55° C., then heating at 85° C. to prepare a tissue lysate, then with the tissue lysate, performing a PCR assay for each gene to measure whether the gene is a wild-type, hetero-deficient type or homo-deficient type or the like, using the following primers.
(1) Primer for Fcer1g test (SEQ ID NO: 1)
5'-CTCGTGCTTTACGGTATCGCC-3'

(Primer 1 for Fcer1g test)

(SEQ ID NO: 2)
5'-CCTACTCTACTGTCGACTCAAG-3'

(Primer 2 for Fcer1g test)

(SEQ ID NO: 3)
5'-GGCTGGCTATAGCTGCCTTTC-3'

(Primer 3 for Fcer1g test)

PCR Reaction Mixture for Fcer1g Test 12.5 μL Buffer for Go-Taq×2
1.0 μL Primer 1 for Fcer1g test (5 μM)
1.0 μL Primer 2 for Fcer1g test (5 μM)
1.0 μL Primer 3 for Fcer1g test (5 μM)
8.0 μL Distilled H$_2$O
1.5 μL Genomic DNA (tissue lysate)
The above reagents were mixed to prepare a PCR reaction mixture.

PCR Amplification Condition

The amplification was performed using 25 μL of the aforementioned PCR reaction mixture in the condition of carrying out heat treatments of 94° C. for 3 minutes; a cycle of 94° C. for 30 seconds, 63° C. for 30 seconds, and 72° C. for 1 minute for 35 cycles; and then 72° C. for 3 minutes. The PCR product obtained by the above PCR was subjected to electrophoresis in a 2% agarose gel, and the presence or absence of a band of the amplified product near the target band size was confirmed to determine whether the target gene in each mouse was the wild-type or KO-type. That is, the above PCR product was determined to be Fcer1g KO when the band size was 240 bp, and Fcer1g wild type(+) when the band size was 198 bp.
(2) Primer for Fcgr2b test (SEQ ID NO: 4)
5'-CTCGTGCTTTACGGTATCGCC-3'

(Primer 1 for Fcgr2b test)

(SEQ ID NO: 5)
5'-AAACTCGACCCCCCGTGGATC-3'

(Primer 2 for Fcgr2b test)

(SEQ ID NO: 6)
5'-TTGACTGTGGCCTTAAACGTGTAG-3'

(Primer 3 for Fcgr2b test)

PCR Reaction Solution for Fcgr2b Test 12.5 μL Buffer for Go-Taq×2
1.0 μL Primer 1 for Fcgr2b test (5 μM)
1.0 μL Primer 2 for Fcgr2b test (5 μM)
1.0 μL Primer 3 for Fcgr2b test (5 μM)
8.0 μL Distilled H$_2$O
1.5 μL Genomic DNA (tissue lysate)
The above reagents were mixed to prepare a PCR reaction solution.

PCR Amplification Condition

The amplification treatment was performed using 25 μL of the above PCR reaction lysate in the condition of carrying out heat treatments of 94° C. for 3 minutes; a cycle of 94° C. for 30 seconds, 63° C. for 30 seconds, and 72° C. for 1 minute for 35 cycles; and then 72° C. for 3 minutes. The PCR product obtained by the above PCR was subjected to electrophoresis in a 2% agarose gel, and the presence or absence of a band of the amplified product near the target band size was confirmed to determine whether the target gene in each mouse was the wild-type or KO-type. That is, the above PCR product was determined to be Fcgr2b KO when the band size was 232 bp, and Fcgr2b wild type(+) when the band size was 161 bp.

(3) Primer for IL-2rg test (SEQ ID NO: 7)
5'-CTGCTCAGAATGCCTCCAATTCC-3'

(Primer 1 for IL-2rg test)

(SEQ ID NO: 8)
5'-CCTCCGTGCAATCCATCTTGTTCAAT-3'

(Primer 2 for IL-2rg test)

(SEQ ID NO: 9)
5'-GATCCAGATTGCCAAGGTGAGTAG-3'

(Primer 3 for IL-2rg test)

PCR Reaction Mixture for IL-2rg Test 7.5 μL PCR buffer (with dNTP, MgCl$_2$)×2 buffer
0.15 μL Primer 1 for IL-2rg test (20 μM)
0.15 μL Primer 2 for IL-2rg test (20 μM)
0.15 μL Primer 3 for IL-2rg test (20 μM)
0.3 μL Tks Gflex DNA polymerase (1.25 U/μL)
5.25 μL Distilled H$_2$O
1.5 μL Genomic DNA (tissue lysate)

The above reagents were mixed to prepare a PCR reaction mixture.

PCR Amplification Condition

The amplification treatment was performed using 25 μL of the above PCR reaction mixture in the condition of carrying out heat treatments of 94° C. for 3 minutes; a cycle of 98° C. for 10 seconds, 65° C. for 15 seconds, and 68° C. for 30 seconds for 30 cycles; and then 68° C. for 3 minutes. The PCR product obtained by the above PCR was subjected to electrophoresis in a 2% agarose gel, and the presence or absence of a band of the amplified product near the target band size was confirmed to determine whether the wild-type of the target gene in each mouse was KO-type. That is, the PCR product was determined to be IL-2rg KO when the band size was 340 bp, and IL-2rg wild type(+) when the band size was 660 bp.

(4) Primer for scid test (SEQ ID NO: 10)
5'-GCTAGAGAGCTGTTCCAGTT-3'

(Primer 1 for scid test)

(SEQ ID NO: 11)
5'-TTTGAACACACACTGATTCTG-3'

(Primer 2 for scid test)

(SEQ ID NO: 12)
5'-ACGCTAAGC-3'

(Primer 3 for scid test)

(SEQ ID NO: 13)
5'-CGCTATGCT-3'

(Primer 4 for scid test)

PCR Reaction Mixture for Scid Test 5.0 μL Cycleave PCR Reaction Mix×2 buffer
0.2 μL Primer 1 for scid test (10 μM)
0.2 μL Primer 2 for scid test (10 μM)
0.4 μL Primer 3 for scid test (5 μM)
0.4 μL Primer 4 for scid test (5 μM)
0.2 μL ROX Reference Dye II (50×)
3.1 μL Distilled H$_2$O
0.5 μL Genomic DNA (tissue lysate)

The above reagents were mixed to prepare a PCR reaction solution.

PCR Amplification Condition

A multiplex real-time PCR assay was performed using μL of the above PCR reaction solution. The amplification treatment was performed in the condition of carrying out heat treatments of 95° C. for 10 seconds; and a cycle of 95° C. for 5 seconds, 55° C. for 10 seconds, and 72° C. for 31 seconds for 45 cycles. From the Threshold cycles (Ct) values of the amplification reaction, it was determined that it had a Scid mutation when an amplification reaction was observed in Real-time PCR with a combination of the primers 1, 2, and 3 for scid test, and that it had no Scid mutation (wild type(+)) when an amplification reaction was observed in Real-time PCR with a combination of the primers 1, 2, and 4 for scid test.

Example 2

Characteristics of NOG-FcgR KO/KO Mouse

Deletion of IgG Antibody Receptor FcgR

In the NOG-FcgR KO/KO mouse produced above, the examination of whether expression of the FcgR molecule has disappeared or not was performed. The peripheral blood from NOG-FcgR KO/KO mice was collected and treated with an erythrocyte hemolytic reaction solution, and erythrocytes were removed therefrom to obtain a leukocyte fraction. After the leukocyte fraction was antibody-stained using fluorochrome-labeled antigen-specific antibodies as shown below, the fluorescence intensity was measured by flow cytometry (device name: BD LSRFortessa™ X-20, manufactured by Becton, Dickinson and Company) to examine the presence or absence of mouse FcgRIII/II (mCD16/32) in mouse CD45 (mCD45)$^+$ leukocytes and the expression of mFceRI molecules and the frequency in mCD45$^+$ leukocytes. Similar experiments were performed on the above NOG-FcgR KO/+ and NOG mice for comparison. The results are shown in FIGS. 1 and 2.

The fluorochrome-labeled antigen-specific antibody and the FcgR blocking antibody for suppressing non-specific binding of antibody used here are as follows:
- PE/Cy7-labeled anti-mouse CD16/32 (FcgRIII/II) antibody (BioLegend Inc.),
- APC/Cy7-labeled anti-mouse CD45 antibody (BioLegend Inc.)

Results

Hereafter, in the description of the Examples and drawings, the NOG mouse is sometimes referred to as "+/+," the NOD-scid, il2rg$^{null}$-Fcer1g$^{null/+}$Fcgr2b$^{null/+}$ (NOG-FcgR KO/+) mouse as "KO/+," and the NOD-scid, il2rg$^{null}$-Fcer1g$^{null/null}$, Fcgr2b$^{null/null}$ (NOG-FcgR KO/KO) mouse as "KO/KO."

As is evident from FIG. 1, mFcgRIII and mFcgRII disappeared in mCD45$^+$ leukocytes in the NOG-FcgR KO/KO mouse (KO/KO) (FIG. 1(d)). On the other hand, the expression of mFcgRIII and mFcgRII was confirmed in the NOG mouse (FIG. 1(b)) and the NOG-FcgR KO/+ mouse (FIG. 1(c)). Similar results were also shown in FIG. 2.

Example 3

Human IgG Antibody Binding Ability

Whether the binding ability to a human IgG antibody was eliminated or not due to the disappearance of expression of the FcgR molecule was examined in the NOG-FcgR KO/KO mouse. Following intraperitoneal administration of 100 μg of a human IgG antibody drug trastuzumab to the NOG-FcgR KO/KO mouse, peripheral blood was collected on day 3 to obtain a leukocyte fraction in a similar manner to Example 2. After the leukocyte fraction was antibody-stained using fluorochrome-labeled antigen-specific antibodies as shown below, the fluorescence intensity was measured by flow cytometry with the aforementioned device to examine expression of FcgRIII/II (mCD16/32) and the presence or absence of binding of the human IgG antibody in a F4/80$^+$CD11b$^+$ monocyte/macrophage fraction in mCD45$^+$ leukocytes. Similar experiments were performed on the NOG-FcgR KO/+ mouse for comparison. In addition, an NOG-FcgR KO/+ mouse to which the human IgG antibody drug described above was not administered was used as a negative control. The results are shown in FIG. 3.

The fluorochrome-labeled antigen-specific antibodies used here are as follows:
- AlexaFluor 488-labeled anti-human IgG Fc antibody (BioLegend Inc.),
- PE-labeled anti-mouse CD11b antibody (BioLegend Inc.),
- PE/Cy7-labeled anti-mouse CD16/32 (FcgRIII/II) antibody (BioLegend Inc.),
- APC-labeled anti-mouse F4/80 antibody (eBioscience, Inc.)
- APC/Cy7-labeled anti-mouse CD45 antibody (BioLegend Inc.)

Results

As is evident from FIG. 3(c), in the human antibody-receiving NOG-FcgR KO/KO mouse, no positive fraction of human FcgRIII/II and no human IgG antibodies were detected in the F4/80$^+$CD11b$^+$ monocyte/macrophage fraction in mCD45$^+$ leukocytes, and thus no binding of human IgG and mouse FcgR was confirmed. On the other hand, as is evident from FIG. 3(b), in the NOG-FcgR KO/+ mouse to which a human IgG antibody was administered, a fraction of human IgG+ was detected in FcgRIII/II positive cells in the mCD45$^+$ F4/80$^+$CD11b$^+$ monocyte/macrophage fraction, and thus it was confirmed that the administered human IgG was bound to mouse FcgR. Meanwhile, in the negative control, FcgRIII/II was positive, but no human IgG antibody was detected (FIG. 3(a)). From the above, it was confirmed that in the NOG-FcgR KO/KO mouse, the antibody binding ability to human IgG antibody was eliminated.

Example 4

Mouse Antibody Metabolic Ability

In the NOG-FcgR KO/KO mouse, whether the metabolic ability of the mouse antibody changes due to the deficiency of the FcgR molecule was examined. To the NOG-FcgR KO/KO mouse, 100 μg or 20 μg of the mouse IgG1 monoclonal antibody (mIgG1, clone MOPC-21) was administered intraperitoneally, and then blood was collected for 12 weeks to obtain a plasma fraction. The concentrations of the mouse IgG antibody in the obtained plasma were measured by ELISA method using a mouse IgG ELISA Quantitation set (manufactured by Bethyl laboratories, Inc). Similar experiments were performed on the NOG mouse and NOG-FcgR KO/+ mouse for comparison. The results are shown in FIG. 4.

Results

As is evident from FIG. 4(b), when 100 μg of the mouse IgG1 antibody was administered to the NOG-FcgR KO/KO mouse, the mouse IgG1 antibody reached its maximum concentration in plasma at week 1 after administration and then decreased gradually, but was detected even at week 12. No difference was observed in antibody concentration even when compared to those in the NOG and NOG-FcgR KO/+ mice (FIG. 4(a)). Thus, it was confirmed that deficiency of the FcgR molecule in the NOG-FcgR KO/KO mouse did not affect the metabolic rate of the mouse antibody. Furthermore, focusing only on the NOG-FcgR KO/KO mouse, and comparing the 100 μg administration group and the 20 μg administration group of mouse IgG1, the 20 μg administration group had a lower antibody concentration in plasma, thus it was confirmed that mouse IgG concentration in plasma was dependent on the amount of antibody administered (FIG. 4(c)).

Example 5

Human Antibody Metabolic Ability

In the NOG-FcgR KO/KO mouse, whether the metabolic ability of the human antibody changes due to the deficiency of the FcgR molecule was examined. To the NOG-FcgR KO/KO mouse, 100 μg each of the three commercially-available antibody drugs shown below as human IgG monoclonal antibodies were administered intraperitoneally, then blood was collected over a period of 28 days to obtain a plasma fraction. The concentrations of each human IgG antibody in the obtained plasma was measured by ELISA method using a human IgG ELISA Quantitation set (manufactured by Bethyl laboratories, Inc). Similar experiments were performed on the NOG-FcgR KO/+ mouse and NOG mouse for comparison. The results are shown in FIG. 5.

The antibody drugs used here are as follows.

Rituximab: anti-CD20 monoclonal antibody: Rituxan (manufactured by Chugai Pharmaceutical Co., Ltd.);

Trastuzumab: anti-HER2 humanized monoclonal antibody Herceptin (Her2 specific antibody pharmaceutical) (manufactured by Chugai Pharmaceutical Co., Ltd.);

Mogamulizumab: humanized anti-CCR4 monoclonal antibody Poteligeo (manufactured by Kyowa Kirin Co., Ltd.);

Results

As is evident from FIGS. 5(a) to (c), administration of each 100 µg of the three human monoclonal antibodies to the NOG-FcgR KO/KO mouse resulted in almost disappearance of any of the human IgG antibodies within 2 weeks after administration. The same tendency was observed in the NOG mouse and NOG-FcgR KO/+ mouse for all of the above three antibodies. Thus, it was confirmed that FcgR deficiency in the NOG-FcgR KO/KO mouse did not affect the metabolic rate of human antibodies either.

Example 6

(Loss of ADCC Activity by Mouse Phagocyte (1))

It is known that phagocytosis is induced by mouse phagocytes recognizing, via mouse FcgR, antigen-specific antibodies that are administered to the NOG mice. Human solid cancer cell lines were then used in the NOG-FcgR KO/KO mouse to examine whether mouse FcgR deficiency eliminates ADCC activity by mouse phagocytes or not.

A 3 mm squared tumor mass of a Her2-positive gastric cancer cell line 4-1ST, one of the human solid cancer cell lines, was subcutaneously transplanted into the NOG-FcgR KO/KO mouse to prepare a 4-1ST-subcutaneously transplanted NOG-FcgR KO/KO mouse. A similar treatment was performed on the NOG-FcgR KO/+ mouse to prepare a 4-1ST-subcutaneously transplanted NOG-FcgR KO/+ mouse for comparison. To each of the 4-1ST-subcutaneously transplanted mice, 50 µg of trastuzumab was administered intraperitoneally, twice a week, from 1 week after 4-1ST transplantation, and tumor size was measured successively over a period of 22 days. To the above two types of the mice, PBS was administered instead of the antibody to prepare a PBS administered control group. The results are shown in FIG. 6.

Result 1

As is evident from FIG. 6(b), in the 4-1ST-subcutaneously transplanted NOG-FcgR KO/KO mouse, the tumor size on day 22 when trastuzumab was administered was on average 850 mm$^3$. On the other hand, in the 4-1ST-subcutaneously transplanted NOG-FcgR KO/+ mouse, the tumor size on day 22 when trastuzumab was administered was on average 150 mm$^3$. Thus, it was confirmed that there is a tumor-suppression effect by trastuzumab antibody administration in the 4-1ST-subcutaneously transplanted NOG-FcgR KO/+ mouse compared to the 4-1ST-subcutaneously transplanted NOG-FcgR KO/KO mouse. Such results indicate that a mouse phagocyte recognizes via mouse FcgR and injures a tumor (human solid cancer) bound to a cancer antigen-specific human antibody to suppress tumor mass growth, and that ADCC activity by a mouse phagocyte is not elicited in the NOG-FcgR KO/KO mouse.

Result 2

As is evident from FIG. 6(a), in the PBS administration control group (saline), no difference in tumor mass growth rates was observed between the 4-1ST-subcutaneously transplanted NOG-FcgR KO/+ mouse and 4-1ST-subcutaneously transplanted NOG-FcgR KO/KO mouse, and it was confirmed that the presence or absence of mouse FcgR does not affect tumor growth rate.

Example 7

(Loss of ADCC Activity by Mouse Phagocyte (2))

A human leukemia cell line was used in the NOG-FcgR KO/KO mouse to examine whether mouse FcgR deficiency eliminates ADCC activity by mouse phagocytes or not. Into the NOG-FcgR KO/KO mouse, $2.4 \times 10^6$ of the CD20$^+$ Burkitt lymphoma lines Daudi, one of the human leukemia cell lines, were transplanted from the tail vein to prepare a Daudi-transplanted NOG-FcgR KO/KO mouse. Similar treatments were performed on the NOG mouse and NOG-FcgR KO/+ mouse to prepare a Daudi-transplanted NOG mouse and a Daudi-transplanted NOG-FcgR KO/+ mouse for comparison.

To each of the mice described above, 50 µg of Rituximab as an antigen-specific antibody drug was administered intraperitoneally from the tail vein once a week. The blood was collected periodically, and CD20$^+$ Daudi cells in the blood were then measured by flow cytometry after antibody-staining. To each of the mice described above, PBS was administered instead of the antibody to prepare a PBS administration control group. The results on day 21 after transplantation are shown in FIG. 7.

Results

As is evident from FIG. 7(b), in the Rituximab-administered, Daudi-transplanted NOG-FcgR KO/KO mouse, CD20$^+$ Daudi cells in the blood were detected at a frequency of 1 to 2% in total leukocytes. On the other hand, in the Rituximab-administered, Daudi-transplanted NOG-FcgR KO/+ mouse, CD20$^+$ Daudi cells in the blood decreased to less than or equal to 0.2% in total leukocytes. Meanwhile, as is evident from FIG. 7(a), in the PBS administration control group, CD20$^+$ Daudi cells in the blood were detected at a frequency of about 1.5% to about 4% in total leukocytes in any of the Daudi-transplanted NOG-FcgR KO/KO mouse, Daudi-transplanted NOG-FcgR KO/+ mouse, and Daudi-transplanted NOG mouse.

Example 8

(Loss of ADCC Activity by Mouse Phagocyte (3))

The Rituximab or PBS-administered, Daudi-transplanted NOG-FcgR KO/KO, Daudi-transplanted NOG-FcgR KO/+, and Daudi-transplanted NOG mice described above were collected after euthanization on day 23 after Daudi transplantation, and their kidneys accumulated by Daudi cells were excised, and the organ weight was measured to evaluate whether ADCC activity of mouse phagocytes was functioning or not. For the results, a photograph of kidneys of each mouse is shown in FIG. 8(a), and a graph of kidney weights of each mouse is shown in FIG. 8(b).

Results

As is evident from FIGS. 8(a) and (b), in the Rituximab administration group (Rit.), the kidney weight increased to around 0.5 g in the Daudi-transplanted NOG-FcgR KO/KO mouse. On the other hand, the kidney weight was around 0.2 g, and the kidney hypertrophy was suppressed in the Daudi-transplanted NOG-FcgR KO/+ mouse. In the PBS administration control group, the kidney weight increased to around 0.5 g in both of the Daudi-transplanted NOG-FcgR KO/+ mouse and the Daudi-transplanted NOG-FcgR KO/KO mouse, and also increased to about 0.57 g in the Daudi-transplanted NOG mouse, and the kidney swelling by Daudi accumulation was observed in all cases. It should be noted that the kidneys of adult NOG mice are known to be generally around 0.2 g. The above results indicate that in the NOG-FcgR KO/KO mouse, even when the antigen-specific antibody Rituximab is administered, mouse phagocytes are unable to recognize and attack cancer cells, Daudi cells, via mouse FcgR.

Summary for ADCC Activity

The results of Examples 6 to 8 suggest that mouse FcgR deficiency in the NOG-FcgR KO/KO mouse results in non-functionality of ADCC activity by mouse phagocytes.

Example 9

Verification of Human Hematopoietic Stem Cell Engraftment Capacity 1

Engraftment capacity of human hematopoietic stem cells in the NOG-FcgR KO/KO mouse was examined.

Preparation of Human Hematopoietic Stem Cell-Transplanted NOG-FcgR KO/KO Mice

An adult NOG-FcgR KO/KO mouse older than or equal to 7 weeks was irradiated with X-rays (Day 0) to suppress bone marrow. Within 1 day after X-ray irradiation, 50,000 hCD34$^+$ human hematopoietic stem cells were transplanted from the tail vein to prepare a human hematopoietic stem cell-transplanted NOG-FcgR KO/KO mouse. Similar preparation treatments as described above were performed on the NOG mouse and the NOG-FcgR KO/+ mouse to prepare a human hematopoietic stem cell-transplanted NOG mouse and a human hematopoietic stem cell transplanted NOG-FcgR KO/+ mouse for comparison.

Examination by Flow Cytometry

For each of the mice, peripheral blood was collected 4, 8, 12, 16, and 20 weeks after human hematopoietic stem cell transplantation to obtain a leukocyte fraction in a similar manner as in Example 2. After the leukocyte fraction was antibody-stained using fluorochrome-labeled antigen-specific antibodies as shown below, the frequency of human immune cells hCD45$^+$ cells was measured by measuring fluorescence intensity by flow cytometry. The results are shown in FIG. 9.

The fluorochrome-labeled antigen-specific antibodies used in Examples 9 to 12 are as follows.

BUV395-labeled anti-hCD33 antibody (Becton, Dickinson and Company)
Brilliant Violet 421-labeled anti-hCD3 antibody (BioLegend, Inc.)
PE/Cy7-labeled anti-hCD19 antibody (BioLegend, Inc.)
APC/R700-labeled anti-hCD56 antibody (Becton, Dickinson and Company)
APC/Cy7-labeled anti-mouse CD45 antibody (BioLegend, Inc.)
Brilliant Violet 510-labeled anti-hCD45 antibody (BioLegend, Inc.)

Results

As is evident from FIGS. 9(a) and (b), the frequency of hCD45$^+$ cells in total leukocytes increased over time in both male (a) and female (b) of the human hematopoietic stem cell-transplanted NOG-FcgR KO/KO mouse, the human hematopoietic stem cell-transplanted NOG mouse and the human hematopoietic stem cell-transplanted NOG-FcgR KO/+ mouse, confirming the engraftment of hCD45$^+$ cells. The engraftment of hCD45$^+$ cells in the human hematopoietic stem cell-transplanted NOG-FcgR KO/KO mouse was significantly greater than that in the mouse for comparison over 8 to 16 weeks. Furthermore, the value was around 75% 20 weeks after human hematopoietic stem cell transplantation, which was significantly higher than that in the mouse for comparison. On the other hand, in the NOG mouse and NOG-FcgR KO/+ mouse, the frequency of hCD45$^+$ cells remained at around 60% even 20 weeks after human hematopoietic stem cell transplantation.

Example 10

Examination of Human Hematopoietic Stem Cell Engraftment Capacity 2

For the human hematopoietic stem cell-transplanted NOG-FcgR KO/KO mouse, the human hematopoietic stem cell-transplanted NOG mouse, and the human hematopoietic stem cell-transplanted NOG-FcgR KO/+ mouse, hCD45$^+$ cells in total leukocytes for 4 weeks to 20 weeks after human hematopoietic stem cell transplantation were examined in detail. The results are shown in FIG. 10.

Results

As is evident from FIG. 10, fractions of hCD33$^+$ myeloid cells (male (a), female (d)), hCD19$^+$ B cells (male (b), female (e)), hCD3$^+$ T cells (male (c), female (f)) were detected in each of the mice described above. Thus, it was confirmed that the deficiency of mouse FcgR does not affect the differentiation ability of human immune cells.

Example 11

Examination of Human Hematopoietic Stem Cell Engraftment Capacity 3

The above human hematopoietic stem cell-transplanted, NOG-FcgR KO/KO mouse, NOG mouse and NOG-FcgR KO/+ mouse were collected after euthanization 26 weeks after human hematopoietic stem cell transplantation, and the extent of engraftment of hCD45$^+$ cells in hematopoietic organs (bone marrow, spleen, blood) was examined by measuring fluorescence intensity by flow cytometry. The results are shown in FIG. 11.

Results

As is evident from FIGS. 11(a) to (f), 26 weeks after human hematopoietic stem cell transplantation, the frequency of hCD45+ cells in bone marrow (BM) ((a) (d)), spleen (Spl) ((b) (e)), blood (PB) ((c) (f)) (Human CD45+ in MNC (%), and cell number (Abs. cell number ($\times 10^6$ cells) or Abs. cell number ($\times 10^3$ cells/μL)) were not significantly different among the human hematopoietic stem cell-transplanted, NOG-FcgR KO/KO mouse, NOG mouse, and NOG-FcgR KO/+ mouse.

Example 12

Examination of Human Hematopoietic Stem Cell Engraftment Capacity 4

For each of the mice collected after euthanization, the frequency of hCD3+ T cells, hCD19+ B cells, hCD33+ myeloid cells, hCD56+ NK cells (Freq. of hCD45(%)) in hCD45+ cells in hematopoietic organs (bone marrow, spleen, blood), and the number of cells in 1 μL of blood (Abs. cell number ($\times 10^3$ cells/μL)) were examined. The results of 2-way ANOVA analysis are shown in FIG. 12.

Results

As is evident from FIG. 12, all the fractions of hCD33+ myeloid cells, hCD19+ B cells, hCD3+ T cells and hCD56+ NK cells were detected in the aforementioned human hematopoietic stem cell-transplanted NOG-FcgR KO/KO mouse, the human hematopoietic stem cell-transplanted NOG mouse and the human hematopoietic stem cell-transplanted NOG-FcgR KO/+ mouse. Particularly for hCD19+ B cells in spleen (e), the cell number detected in the human hematopoietic stem cell-transplanted NOG-FcgR KO/KO mouse was significantly high, that is, 2.5 or more times greater than that in the NOG mice and 1.2 or more times greater than that in the KO/+ mice.

Example 13

Differentiation of T Cell Subpopulation

It is generally known that hCD3+ T cells are further divided into subpopulations of CD4+ T cells, CD8+ T cells, CD4+ CD8+ double positive (DP) T cells. The differentiation of T cell subpopulations was then evaluated for the aforementioned human hematopoietic stem cell-transplanted, NOG-FcgR KO/KO mouse, NOG mouse and NOG-FcgR KO/+ mouse by measuring fluorescence intensity by flow cytometry for collected peripheral blood samples after antibody-staining with fluorochrome-labeled antigen-specific antibodies shown below. The results are shown in FIG. 13.

The fluorochrome-labeled antigen-specific antibodies used here are as follows.
PE-labeled anti-hCD4 antibody (BioLegend, Inc.)
PE/Cy7-labeled anti-hCD8a antibody (BioLegend, Inc.)
Brilliant Violet 421-labeled anti-hCD3 antibody (BioLegend, Inc.)
Brilliant Violet 510-labeled anti-hCD45 antibody (BioLegend, Inc.)
Brilliant Violet 605-labeled anti-human PD-1 (CD279) antibody (BioLegend, Inc.)

Results

As is evident from FIG. 13, subpopulations of hCD4+ T cells, hCD8+ T cells, hCD4+ hCD8+ hDP T cells were normally differentiated in any of the human hematopoietic stem cell-transplanted NOG-FcgR KO/KO mouse, NOG mouse and NOG-FcgR KO/+ mouse, confirming the reconstitution of a blood immune system (FIG. 13(a)). Furthermore, from the observation of expression of the programmed cell death 1 (PD-1) protein molecule expressed in human T cells, it was confirmed that hPD-1 molecules were further expressed in the hCD4+ fraction (FIG. 13(b)).

Thus, it was confirmed that FcgR deficiency does not affect these functions.

Example 14

Examination of Mouse ADCC Activity on Human Immune Cells in Human Blood Immune System-Reconstituted NOG-FcgR KO/KO Mouse An adult NOG-FcgR KO/KO mouse older than or equal to 7 weeks was irradiated with X-rays to suppress bone marrow. Within 1 day after X-ray irradiation, 50,000 human hematopoietic stem cells were transplanted from the tail vein to prepare a human hematopoietic stem cell-transplanted NOG-FcgR KO/KO mouse. For the mouse confirmed differentiation of hCD3+ T cells 16 weeks after human hematopoietic cell transplantation, 100 μg each of anti-human PD-1 antibody (OPDIVO) (manufactured by Bristol-Myers Squibb) that specifically recognizes a PD-1 protein molecule expressed in human T cells were administered once a week in 18th weeks, 19th weeks, and 20th weeks after human hematopoietic stem cell transplantation, a total of 3 times, and then the mouse was collected after euthanization and analyzed by flow cytometry for increase or decrease of human immune cells including human T cells in each hematopoietic tissue of bone marrow, spleen, and blood. Similar treatments were performed on the human hematopoietic stem cell-transplanted NOG mouse and human hematopoietic stem cell-transplanted NOG-FcgR KO/+ mouse for comparison. The results are shown in FIG. 14.

The fluorochrome-labeled antigen-specific antibodies used herein are as follows.
PE-labeled anti-hCD4 antibody (BioLegend, Inc.)
PE/Cy7-labeled anti-hCD8a antibody (BioLegend, Inc.)
PE/Cy7-labeled anti-hCD19 antibody (BioLegend, Inc.)
APC-R700-labeled anti-hCD19 antibody (Becton, Dickinson and Company)
APC-R700-labeled anti-hCD56 antibody (Becton, Dickinson and Company)
Brilliant Violet 421-labeled anti-hCD3 antibody (BioLegend, Inc.)
Brilliant Violet 510-labeled anti-hCD45 antibody (BioLegend, Inc.)
Brilliant Violet 605-labeled anti-human PD-1 (CD279) antibody (BioLegend, Inc.)
BUV395-labeled anti-hCD33 antibody (Becton, Dickinson and Company)
APC/Cy7-labeled anti-mouse CD45 antibody (BioLegend, Inc.)

Results

As is evident from FIGS. 14(a) to (c), no significant difference was observed in any organ with respect to the frequency of hCD45+ cells in bone marrow, spleen, and blood (hCD45+ in MNC (%)) of each of the OPDIVO-administered mice. On the other hand, as is evident from FIG. 14(e), in spleen, the number of hCD45+ cells (Abs. cell number ($\times 10^6$ cells)) detected in the OPDIVO-administered human hematopoietic stem cell-transplanted NOG-FcgR KO/KO mouse was 4.2 times greater than that in the OPDIVO-administered, human hematopoietic stem cell-transplanted NOG mouse and 2.2 or more times greater than that in human hematopoietic stem cell-transplanted NOG-FcgR KO/+ mouse, indicating that, in the NOG-FcgR KO/KO mouse, hCD45+ cells were engrafted without decreasing in cell number.

Example 15

Each of the OPDIVO-administered, human hematopoietic stem cell-transplanted mouse described above was analyzed to examine details of hCD45+ cells. The results are shown in FIG. 15.

Results

As is evident from FIG. 15, each fraction of hCD3+ T cells, hCD19+ B cells, hCD33+ myeloid cells, hCD56+ NK cells was detected in all of OPDIVO-administered mice described above. Furthermore, in the OPDIVO-administered human hematopoietic stem cell-transplanted NOG-FcgR KO/KO mouse, hCD3+ T cells were engrafted in the spleen (FIG. 15(b)) and peripheral blood (FIG. 15(c)) without decreasing, and the frequency of hCD3+ T cells was two or more times greater than that in the NOG mouse. Furthermore, in the spleen (FIG. 15(e)), the number of hCD3+ T cells was three or more times greater than that in the NOG mouse, and the hCD19+ B cells were also three or more times greater than those in the NOG mouse.

Example 16

For the detected hCD3+ T cells in hCD45+ cells in the spleen described above, a subset of T cells was further examined. The results are shown in FIG. 16.

Results

As is evident from FIG. 16, the OPDIVO-administered, human hematopoietic stem cell-transplanted NOG-FcgR KO/KO mouse had a significantly higher frequency of hCD4+ T cells in hCD45+ cells in the spleen compared to the OPDIVO-administered, human hematopoietic stem cell-transplanted NOG and human hematopoietic stem cell-transplanted NOG-FcgR KO/+ mice, and the frequency was three or more times greater than that in the NOG mouse and the NOG-FcgR KO/+ mouse. Furthermore, the hCD4+ T cell number was eight or more times greater than that in the NOG mouse and the NOG-FcgR KO/+ mouse, the hCD8+ T cell number was four or more times greater than that in the NOG mouse and the NOG-FcgR KO/+ mouse, and the T cell subset cell number was also significantly large.

Summary of Examples 14 to 16

These results suggest that, in the NOG mouse and the NOG-FcgR KO/+ mouse, hPD-1+ T cells are removed from the mouse living bodies by anti-PD-1 antibodies due to the presence of mouse FcgR molecules, while in the NOG-FcgR KO/KO mouse, the anti-PD-1 antibody-dependent removal of human T cells does not occur because FcgR molecules are deleted.

Example 17

(Examination of Engraftment Capacity of Human Peripheral Blood Derived Monoclonal Cells (PBMCs) Fraction)

The engraftment capacity of human PBMCs in the NOG-FcgR KO/KO mouse was examined. Into an adult NOG-FcgR KO/KO mouse older than or equal to 7 weeks, 1,500,000 or 2,500,000 human PBMCs were transplanted from the mouse tail vein to prepare a human PBMC-transplanted NOG-FcgR KO/KO mouse. Similar preparation treatment was performed on the NOG mouse to prepare a human PBMC-transplanted NOG mouse for comparison.

Examination by Flow Cytometry

For each of the mice, blood was collected 2 weeks, 4 weeks, 5 weeks and/or 6 weeks after human PBMC transplantation to obtain a leukocyte fraction in a similar manner to Example 2. After the leukocyte fraction was antibody-stained using fluorochrome-labeled antigen-specific antibodies as shown below, the frequency of human immune cells, hCD45+ cells, was measured by measuring fluorescence intensity by flow cytometry. The results are shown in FIG. 17.

The fluorochrome-labeled antigen-specific antibodies used herein are as follows.
  FITC-labeled anti-hCD33 antibody (BioLegend, Inc.)
  PE-labeled anti-hCD3 antibody (BioLegend, Inc.)
  PE/Cy7-labeled anti-hCD19 antibody (BioLegend, Inc.)
  APC-labeled anti-mouse CD45 antibody (BioLegend, Inc.)
  APC/Cy7-labeled anti-hCD45 antibody (BioLegend, Inc.)
  FITC-labeled anti-hCD4 antibody (BioLegend, Inc.)
  PE/Cy7-labeled anti-hCD19 antibody (BioLegend, Inc.)
  APC-labeled anti-hCD19 antibody (BioLegend, Inc.)
  APC-R700-labeled anti-hCD56 antibody (Becton, Dickinson and Company)
  APC/Cy7-labeled anti-mouse CD45 antibody (BioLegend, Inc.)
  Brilliant Violet 421-labeled anti-hCD3 antibody (BioLegend, Inc.)
  Brilliant Violet 510-labeled anti-hCD45 antibody (BioLegend, Inc.)

Results

As is evident from FIGS. 17(a) and (b), engraftment of hCD45+ cells was confirmed in both of the 2,500,000-human PBMC-transplanted NOG-FcgR KO/KO mouse and the human PBMC-transplanted NOG mouse. However, the human cell engraftment ratio in total leukocytes was on average around 10% at week 4 in the human PBMC-transplanted NOG mouse, while on average 48% at week 4 in the human PBMC-transplanted NOG-FcgR KO/KO mouse, showing the value of 3.5 or more times greater than that in the NOG mouse at such early time, week 4. Furthermore, when the number of transplanted cells was reduced to 1,500,000 human PBMCs and the evaluation was performed at week 2, as is evident from FIG. 17(c), human cell engraftment ratio in total leukocytes was less than 0.5% in the human PBMC-transplanted NOG mouse, while 1 to 8% in the human PBMC-transplanted NOG-FcgR KO/KO mouse, that was 2 to 16 times greater than that in the NOG mouse. Furthermore, as is evident from FIG. 17(d), the engrafted cell number was 50 to 200/μL in the human PBMC-transplanted NOG-FcgR KO/KO mouse, while around 10/μL in the human PBMC-transplanted NOG mouse. Thus, it was confirmed that the engraftment capacity was significantly higher in the human PBMC-transplanted NOG-FcgR KO/KO mouse compared to that in the human PBMC-transplanted NOG mouse, particularly in the early period after PBMC transplantation, and even when the number of transplanted PBMC cells is smaller than that in conventional practice.

Example 18

Human PBMC Engraftment Capacity

For the human PBMC-transplanted NOG-FcgR KO/KO mouse and human PBMC-transplanted NOG mouse described above, hCD45$^+$ cells in peripheral blood were examined, in detail, in 4 weeks after human PBMC transplantation. The results are shown in FIG. 18.

The fluorochrome-labeled antigen-specific antibodies used herein are as follows.
  FITC-labeled anti-hCD4 antibody (BioLegend Inc.)
  PE/Cy7-labeled anti-hCD3 antibody (BioLegend Inc.)
  APC/Cy7-labeled anti-hCD45 antibody (BioLegend Inc.)
  PE/Cy7-labeled anti-hCD19 antibody (BioLegend Inc.)
  APC-labeled anti-hCD8a antibody (BioLegend Inc.)
  APC-R700-labeled anti-hCD56 antibody (Becton, Dickinson and Company)
  APC/Cy7-labeled anti-mouse CD45 antibody (BioLegend Inc.)
  Brilliant Violet 421-labeled anti-hCD3 antibody (BioLegend Inc.)
  Brilliant Violet 510-labeled anti-hCD45 antibody (BioLegend Inc.)

Results

As is evident from FIGS. 18(a) and (c), it was confirmed that hCD3$^+$ T cells constitute 97% or more of hCD45$^+$ cells in the human PBMC-transplanted NOG-FcgR KO/KO mouse. In the 1,500,000-human PBMC-transplanted NOG mouse, the frequency of hCD3$^+$ T cells was approximately 75%. As is evident from FIGS. 18(b) and (d), for the T cell subpopulations, every fraction of CD4$^+$ T cells, CD8$^+$ T cells, and CD4$^+$CD8$^+$ DP T cells was detected in all of the above human PBMC-transplanted mice.

Example 19

Antibody Reactivity on Human Immune Cells in Human PBMC-Transplanted NOG-FcgR KO/KO Mouse Flow cytometry analysis of hCD3$^+$ T cells showed that PD-1 molecules were expressed in most of the human PBMC-derived hCD3$^+$ cells proliferated in the human PBMC-transplanted NOG mouse and the human PBMC-transplanted NOG-FcgR KO/+ mouse, and that PD-1 molecules were also expressed in the human PBMC-transplanted NOG-FcgR KO/KO mouse (FIG. 19(a)). Furthermore, 50 μg each of the anti-human PD-1 antibody (mouse IgG1 type (clone J116)) was administered to each of the mice at 5th week, 6th week, and 7th week after PBMC transplantation to examine whether cytotoxicity to human PD-1$^+$ T cells was induced or not. The results are shown in FIG. 19(b).

Results

As is evident from FIG. 19(b), in the NOG-FcgR KO/KO mouse, administration of the anti-human PD-1 antibody (mouse IgG1 type) did not result in a decrease in the frequency of human T cells in hCD45$^+$ cells. On the other hand, in the human PBMC-transplanted NOG mouse and the human PBMC-transplanted NOG-FcgR KO/+ mouse, the frequency of human T cells in hCD45$^+$ cells was very low. Thus, it was confirmed that, in the NOG-FcgR KO/KO mouse, anti-human PD-1 antibody-dependent depletion of human T cells does not occur because FcgR molecules are deleted.

Example 20

Establishment of Hybrid Animal Model

The NOG-FcgR KO/KO mouse was crossed with an NOG-hIL-15 Tg mouse capable of expanding and retaining human NK cells in the mouse living body, in an attempt to generate an animal model having both properties. That is, the NOG-FcgR KO/KO mouse was crossed with the NOG-hIL-15 Tg mouse to generate an NOG-FcgR KO/KO, hIL-15 Tg mouse.

Example 21

(Examination of Engraftment Capacity of Human Peripheral Blood-Derived NK Cells Cultured and Expanded In Vitro (Expanded NK Cells))

The engraftment capacity of human Expanded NK cells in the NOG-FcgR KO/KO, hIL-15 Tg mouse was examined. Into an adult NOG-FcgR KO/KO, hIL-15 Tg mouse older than or equal to 7 weeks, 3,850,000 human Expanded NK cells were transplanted from the mouse tail vein to prepare a human Expanded NK cell-transplanted NOG-FcgR KO/KO, hIL-15 Tg mouse (FcgR KO/KO, hIL-15 Tg). Similar preparation treatment as described above was performed on the NOG-hIL-Tg mouse to prepare a human Expanded NK cell-transplanted NOG-hIL-15 Tg mouse (FcgR+/+, hIL-15 Tg) for comparison.

From the human Expanded NK cell-transplanted NOG-FcgR KO/KO, hIL-15 Tg mouse and the human Expanded NK cell-transplanted NOG-hIL-15 Tg mouse, peripheral blood was collected 2 weeks after human Expanded NK cell transplantation, and the engraftment capacity of hCD45$^+$ cells was examined. The results are shown in FIG. 20.

The fluorochrome-labeled antigen-specific antibodies used here are as follows:
  APC-R700-labeled anti-hCD56 antibody (Becton, Dickinson and Company)
  APC/Cy7-labeled anti-mouse CD45 antibody (BioLegend, Inc.)
  Brilliant Violet 421-labeled anti-hCD3 antibody (BioLegend, Inc.)
  Brilliant Violet 510-labeled anti-hCD45 antibody (BioLegend, Inc.)

Results

As is evident from FIG. 20(a), engraftment of hCD45$^+$ cells was observed in all the above human Expanded NK cell-transplanted mice. Furthermore, as is evident from FIG. 20(b), it was confirmed that hCD56$^+$ NK cells constitute 80% or more of hCD45$^+$ cells. These results suggest that the NOG-FcgR KO/KO hIL-15 Tg mouse possesses the human NK cell-engraftment property with which hCD56+ cells can be detected in vivo for a long time after transplantation of human NK cells derived from human peripheral blood, that is a characteristic of the NOG-hIL-15 Tg mouse.

Into the NOG-FcgR KO/KO, hIL-15 Tg mouse described above, 1,500,000 Daudi were transplanted from the tail vein. Three days after transplantation, 8,500,000 human peripheral blood-derived NK cells cultured in vitro and expanded (Expanded NK cells) were transplanted from the tail vein, and 25 μg of anti-CD20 antibody rituximab, a human antibody drug, was administered intraperitoneally once a week. Three weeks later, the kidney weight was measured and evaluated. Separately, the NOG-hIL-15 Tg mouse was crossed to generate an NOG-FcgR KO/+, hIL-15 Tg mouse, and 1,500,000 Daudi were transplanted into the generated mouse from the tail vein, and 1,500,000 Daudi were also transplanted into the NOG-FcgR KO/+ mouse from the tail vein. Both of the obtained mice were used for comparison. The results are shown in FIG. 21.

As is evident from FIG. 21, in the NOG-FcgR KO/+(−non-Tg) mouse, rituximab administration suppressed the kidney weight. Conversely, in the NOG-FcgR KO/KO, non-Tg mouse, an increase of the kidney weight was observed even in the rituximab administration group. Furthermore, in the NOG-FcgR KO/KO hIL-15 Tg mouse, the kidney weight remained at high level both in NK cell transplantation alone and rituximab administration alone, while swelling of kidney was suppressed in combination of NK cell transplantation and rituximab administration. These results suggest that the NOG-FcgR KO/KO hIL-15 Tg mouse has both of each property of the NOG-FcgR KO/KO mouse and the NOG-hIL-15 Tg mouse, and thus can be used to evaluate ADCC activity on a tumor bound to a cancer antigen-specific human antibody, using only human NK cells as effector cells, without being affected by mouse phagocytes.

Example 22

In the following, the examination is conducted in the genetically modified immunodeficient mouse to find out whether the physiological activity of an anti-human antibody could be further evaluated under the environment where a human immune cell and a human tumor cell co-exist. In other words, the immunodeficient mouse engrafted with a human cell was used to evaluate the activity and mechanism of action of an antibody against human cell surface protein acting as an immune checkpoint inhibitor.

Examination of Enhancing Function of Tumor Suppression Response by Immune Checkpoint Inhibitor The function of a human immune checkpoint inhibitor in the NOG-FcgR KO/KO mouse in which a human blood immune system was reconstituted was evaluated. As the immune checkpoint inhibitor, anti-human PD-1 antibody, nivolumab (manufactured by Bristol Myers Squibb) was used. An adult NOG-FcgR KO/KO mouse in 8 weeks-old or older was irradiated with X-rays to suppress bone marrow, and 50,000 human hematopoietic stem cells were transplanted into the mouse from the tail vein within 1 day after X-ray irradiation to prepare a human hematopoietic stem cell-transplanted NOG-FcgR KO/KO mouse. After 16 weeks or more from human hematopoietic stem cell transplantation, differentiation of human $CD3^+$ T cells was confirmed in the human hematopoietic stem cell-transplanted NOG-FcgR KO/KO mouse, a human head and neck squamous epithelial cancer cell line HSC-4 (1,500,000 cells) was subcutaneously transplanted 24 weeks after the human hematopoietic stem cell transplantation to prepare an HSC-4 transplanted NOG-FcgR KO/KO mouse (day 0 in FIG. 22).

Into the mouse, 200 μg of nivolumab was administered intraperitoneally every week after HSC-4 transplantation. At 7, 14, 21, and 28 days after HSC-4 transplantation, tumor size was measured. Similar procedures as described above were performed on the NOG mouse to prepare a human hematopoietic stem cell-transplanted NOG mouse, and then prepare a HSC-4 transplanted NOG (−FcgR+/+) mouse. Furthermore, to the above two types of the mice, PBS was administered instead the antibody to prepare a PBS administered control group. The results of the tumor size measurement are shown in FIG. 22.

Results

As is evident from FIG. 22(b), in the HSC-4 transplanted NOG-FcgR KO/KO mouse, the tumor size at day 28 when PBS was administered was on average 1300 $mm^3$. On the other hand, the tumor size on day 28 when nivolumab was administered was on average 600 $mm^3$. Thus, a tumor suppressive effect by nivolumab antibody administration was confirmed by comparison to the PBS administration group. Meanwhile, as is evident from FIG. 22(a), in the HSC-4 transplanted NOG-FcgR+/+ mouse, the tumor size at day 28 was on average 1000 $mm^3$ either when PBS was administered or when nivolumab was administered, thus no tumor suppressive effect by nivolumab antibody administration was confirmed. These results showed that, in the HSC-4 transplanted NOG-FcgR KO/KO mouse, a function to enhance tumor suppression response by the immune checkpoint inhibitor was detected, while in the HSC-4 transplanted NOG (−FcgR+/+) mouse, the function to enhance tumor suppression response was not detected. Thus, it was confirmed that physiological activity, such as a function to enhance tumor suppression response, can be evaluated in the HSC-4 transplanted NOG-FcgR KO/KO mouse in which a human immune cell and a human tumor cell co-exist.

Example 23

Examination of Enhancing Function of T Cell Infiltration of Human Immune Checkpoint Inhibitor For the HSC-4 transplanted NOG-FcgR KO/KO mouse described above, blood was collected 28 weeks after human hematopoietic stem cell transplantation, and the mouse was collected after euthanization 28 weeks after human hematopoietic cell transplantation (the day following the last administration of an anti-human PD-1 antibody (nivolumab)), then the spleen and tumor were collected. Increase or decrease of human immune cells, including human T cells, in each tissue of the tumor, spleen and blood was analyzed by flow cytometry. Furthermore, for the blood and spleen, a leukocyte fraction was obtained in a similar manner to Example 2. Similar treatment was performed on the HSC-4 transplanted NOG (−FcgR+/+) mouse for comparison.

The above tumors were minced in RPMI1640 medium (manufactured by Invitrogen) containing 1 mg/mL Collagenase IV (manufactured by Sigma-Aldrich)/100 μg/mL DNase I (manufactured by Sigma-Aldrich), and further incubated at 37° C. for a total of 60 minutes while suspended using gentleMACS dissociator (manufactured by Miltenyi Biotec) to isolate cells. A leukocyte fraction was obtained from the cell suspension. The leukocyte fraction was antibody-stained using fluorochrome-labeled antigen-specific antibodies as shown below, then the frequency of human immune cells, hCD45$^+$CD3$^+$ cells, was measured by measuring the fluorescence intensity by flow cytometry. The results are shown in FIG. 23.

The fluorochrome-labeled antigen-specific antibodies used herein are as follows.
- FITC-labeled anti-hCD44 antibody (BioLegend, Inc.)
- PE-labeled anti-hPD-1 antibody (BioLegend, Inc.)
- PE/Cy7-labeled anti-hCD8a antibody (BioLegend, Inc.)
- PerCP-Cy5.5-labeled anti-mCD45 antibody (BioLegend, Inc.)
- APC-labeled anti-hCD69 antibody (BioLegend, Inc.)
- Alexa Fluor-R700-labeled anti-hCD19 antibody (Becton, Dickinson and Company)
- APC-Cy7-labeled anti-hCD4 antibody (BioLegend, Inc.)
- Brilliant Violet 421-labeled anti-hCD3 antibody (BioLegend, Inc.)
- Brilliant Violet 510-labeled anti-hCD45 antibody (BioLegend, Inc.)
- Brilliant Violet 605-labeled anti-human PD-1 (CD279) antibody (BioLegend, Inc.)

Result 1

As is evident from FIG. 23(a), in the HSC-4-subcutaneously transplanted NOG-FcgR KO/KO mouse, the frequency of human T cells in the mononuclear cell fraction infiltrated into the tumor was 12% on average when PBS was administered, while the frequency of human T cells was 30% when nivolumab was administered. Thus, the enhancement of human T cells infiltrated into the tumor by nivolumab antibody administration was confirmed by comparison to the PBS administration group. On the other hand, in the HSC-4-subcutaneously transplanted NOG-FcgR+/+ mouse, the frequency of human T cells in the mononuclear cell fraction infiltrated into the tumor was 2.3% on average when PBS was administered, while the frequency of human T cells was 0.7% when nivolumab was administered. Thus, a decrease in human T cells into the tumor by nivolumab antibody administration was confirmed by comparison to the PBS administration group. Furthermore, as is evident from FIGS. 23(b) and (c), in the spleen and blood of the HSC-4-subcutaneously transplanted NOG-FcgR KO/KO mouse, the frequency of human T cells was 31.5% on average in the spleen and 20.8% on average in the peripheral blood when nivolumab was administered, while, the rate was 9.8% on average in the spleen and 11.6% on average in the peripheral blood, when PBS was administered. Thus, the frequency of T cells when nivolumab was administered was larger than that in the PBS administration group, and an increase in the frequency of human T cells by nivolumab antibody administration was confirmed. In the HSC-4-subcutaneously transplanted NOG-FcgR+/+ mouse, the frequency of occupied by human T cells was 6.0% on average in the spleen and 1.8% on average in the peripheral blood when nivolumab was administered, while, 9.2% on average in the spleen and 2.8% on average in the peripheral blood, when PBS was administered. Thus, a decrease in the number of human T cells by nivolumab antibody administration was confirmed.

Result 2

As is evident from FIG. 23(d), in the HSC-4-subcutaneously transplanted NOG-FcgR KO/KO mice, the number of human T cells in the tumor was 600,000 on average when PBS was administered, while the number of human T cells in the tumor was 2,100,000 on average when nivolumab was administered. The number of human T cells in the tumor was increased by nivolumab antibody administration compared to the PBS administration group. However, in the HSC-4-subcutaneously transplanted NOG-FcgR+/+ mouse, the number of human T cells in the tumor was 140,000 on average when PBS was administered, while the number of human T cells in the tumor was 36,000 on average when nivolumab was administered. Thus, a decrease in the number of human T cells in the tumor by nivolumab antibody administration was confirmed by comparison to the PBS administration group. As is evident from FIGS. 23(e) and (f), in the spleen and blood of the HSC-4 subcutaneously transplanted NOG-FcgR KO/KO mouse, the number of human T cells was 12,400,000 on average in the spleen and 1,270,000/mL on average in the peripheral blood when nivolumab was administered, while 2,600,000 on average in the spleen and 350,000/mL on average in the peripheral blood, when PBS was administered. Thus, an increase in the number of human T cells by nivolumab antibody administration was confirmed by compared to the PBS administration group. In the HSC-4-subcutaneously transplanted NOG-FcgR+/+ mice, the number of human T cells was 800,000 on average in the spleen and 60,000/mL on average in the peripheral blood when nivolumab was administered, while 2,000,000 on average in the spleen and 190,000/mL on average in the peripheral blood when PBS was administered. Thus, a decrease in the number of human T cells by nivolumab antibody administration was confirmed.

The above results show that, in the NOG (−FcgR+/+) mouse, PD-1$^+$ T cells in the tumor were injured by mouse phagocytes with an anti-PD-1 antibody, while in the NOG-FcgR KO/KO mouse, an enhancing effect of T cell infiltration into the tumor, which is physiological activity of an immune checkpoint inhibitor, was able to be detected.

INDUSTRIAL APPLICABILITY

The mouse of the present invention is very useful in the medical field as a humanized immunodeficient mouse used for evaluating ADCC activity without being affected by mouse phagocytes.

SEQUENCE LISTING

PCT_Immunodeficient Mouse_20190925_101424_0.txt

The invention claimed is:

1. A genetically modified immunodeficient mouse in which a mutation is introduced into the gene of the IL-2 receptor γ chain to disrupt the IL-2 receptor γ chain; which has a mutation of a gene involved in rearrangement of antigen receptor genes of T cells and B cells at both allelic loci; and in which Fcer1g gene and Fcgr2b gene are deficient.

2. The genetically modified immunodeficient mouse according to claim 1, wherein the mutation of the gene involved in rearrangement of the antigen receptor genes of T cells and B cells includes a SCID mutation or a RAG mutation.

3. The genetically modified immunodeficient mouse according to claim 2, wherein the genetically modified immunodeficient mouse is a NOG-FcgR KO mouse.

4. The genetically modified immunodeficient mouse according to claim 2, wherein the genetically modified immunodeficient mouse does not exhibit antibody dependent cellular cytotoxic activity on a tumor.

5. The genetically modified immunodeficient mouse according to claim 2, wherein the genetically modified immunodeficient mouse is engrafted with a human cell.

6. The genetically modified immunodeficient mouse according to claim 1, wherein the genetically modified immunodeficient mouse is a NOG-FcgR KO mouse.

7. The genetically modified immunodeficient mouse according to claim 6, wherein the genetically modified immunodeficient mouse does not exhibit antibody dependent cellular cytotoxic activity on a tumor.

8. The genetically modified immunodeficient mouse according to claim 6, wherein the genetically modified immunodeficient mouse is engrafted with a human cell.

9. The genetically modified immunodeficient mouse according to claim 1, wherein the genetically modified immunodeficient mouse does not exhibit antibody-dependent cellular cytotoxic activity on a tumor.

10. The genetically modified immunodeficient mouse according to claim 9, wherein the genetically modified immunodeficient mouse is engrafted with a human cell.

11. The genetically modified immunodeficient mouse according to claim 1, wherein the genetically modified immunodeficient mouse is engrafted with a human cell.

12. The genetically modified immunodeficient mouse according to claim 11, wherein the human cell is a human peripheral blood mononuclear cell.

13. A method for evaluating activity or a mechanism of action of an antibody, the method comprising administering the antibody into the mouse of claim 12, collecting peripheral blood from the mouse, obtaining a leukocyte fraction from the peripheral blood, and counting human immune cells in the peripheral blood, wherein the antibody is against a human cell surface protein on the human peripheral blood mononuclear cell.

14. A germ cell derived from the immunodeficient mouse engrafted with the human cell according to claim 11.

15. A method for evaluating activity or a mechanism of action of an antibody, the method comprising administering the antibody into the mouse of claim 11, collecting peripheral blood from the mouse, obtaining a leukocyte fraction from the peripheral blood, and counting the human cell in the peripheral blood, wherein the antibody is against a human cell surface protein on the human cell and wherein the human cell is a human leukemia cell.

16. The genetically modified immunodeficient mouse according to claim 1, wherein the mouse further expresses the human IL-15 gene.

17. A method for evaluating antibody-dependent cellular cytotoxic activity of a human NK cell, the method comprising transplanting human expanded NK cells, tumor cells, and an antibody binding the tumor cells into the mouse of claim 16 and measuring the size of a tumor formed by the tumor cells.

18. The genetically modified immunodeficient mouse according to claim 1, wherein the genetically modified immunodeficient mouse is engrafted with a human immune cell and a human tumor cell and wherein the human immune cell and the human tumor cell co-exist in the genetically modified immunodeficient mouse.

* * * * *

SEQUENCE LISTING

<160> NUMBER OF SEQ ID NOS: 13

<210> SEQ ID NO 1
<211> LENGTH: 21
<212> TYPE: DNA

```
<213> ORGANISM: Artificial
<220> FEATURE:
<223> OTHER INFORMATION: Inventor: Takahashi, Takeshi; Katano, Ikumi
<220> FEATURE:
<223> OTHER INFORMATION: Fcer1g primer 1

<400> SEQUENCE: 1
ctcgtgcttt acggtatcgc c                                              21

<210> SEQ ID NO 2
<211> LENGTH: 22
<212> TYPE: DNA
<213> ORGANISM: Artificial
<220> FEATURE:
<223> OTHER INFORMATION: Fcer1g primer2

<400> SEQUENCE: 2
cctactctac tgtcgactca ag                                             22

<210> SEQ ID NO 3
<211> LENGTH: 21
<212> TYPE: DNA
<213> ORGANISM: Artificial
<220> FEATURE:
<223> OTHER INFORMATION: Fcer1g primer3

<400> SEQUENCE: 3
ggctggctat agctgccttt c                                              21

<210> SEQ ID NO 4
<211> LENGTH: 21
<212> TYPE: DNA
<213> ORGANISM: Artificial
<220> FEATURE:
<223> OTHER INFORMATION: Fcgr2b primer1

<400> SEQUENCE: 4
ctcgtgcttt acggtatcgc c                                              21

<210> SEQ ID NO 5
<211> LENGTH: 21
<212> TYPE: DNA
<213> ORGANISM: Artificial
<220> FEATURE:
<223> OTHER INFORMATION: Fcgr2b primer2

<400> SEQUENCE: 5
aaactcgacc ccccgtggat c                                              21

<210> SEQ ID NO 6
<211> LENGTH: 24
<212> TYPE: DNA
<213> ORGANISM: Artificial
<220> FEATURE:
<223> OTHER INFORMATION: Fcgr2b primer3

<400> SEQUENCE: 6
ttgactgtgg ccttaaacgt gtag                                           24

<210> SEQ ID NO 7
<211> LENGTH: 23
<212> TYPE: DNA
<213> ORGANISM: Artificial
<220> FEATURE:
<223> OTHER INFORMATION: IL-2rg primer1

<400> SEQUENCE: 7
```

```
ctgctcagaa tgcctccaat tcc                                          23

<210> SEQ ID NO 8
<211> LENGTH: 26
<212> TYPE: DNA
<213> ORGANISM: Artificial
<220> FEATURE:
<223> OTHER INFORMATION: IL-2rg primer2

<400> SEQUENCE: 8
cctccgtgca atccatcttg ttcaat                                       26

<210> SEQ ID NO 9
<211> LENGTH: 24
<212> TYPE: DNA
<213> ORGANISM: Artificial
<220> FEATURE:
<223> OTHER INFORMATION: IL-2rg primer3

<400> SEQUENCE: 9
gatccagatt gccaaggtga gtag                                         24

<210> SEQ ID NO 10
<211> LENGTH: 20
<212> TYPE: DNA
<213> ORGANISM: Artificial
<220> FEATURE:
<223> OTHER INFORMATION: scid primer1

<400> SEQUENCE: 10
gctagagagc tgttccagtt                                              20

<210> SEQ ID NO 11
<211> LENGTH: 21
<212> TYPE: DNA
<213> ORGANISM: Artificial
<220> FEATURE:
<223> OTHER INFORMATION: scid primer2

<400> SEQUENCE: 11
tttgaacaca cactgattct g                                            21

<210> SEQ ID NO 12
<211> LENGTH: 9
<212> TYPE: DNA
<213> ORGANISM: Artificial
<220> FEATURE:
<223> OTHER INFORMATION: scid primer3

<400> SEQUENCE: 12 acgctaagc                                                           9

<210> SEQ ID NO 13
<211> LENGTH: 9
<212> TYPE: DNA
<213> ORGANISM: Artificial
<220> FEATURE:
<223> OTHER INFORMATION: scid primer4

<400> SEQUENCE: 13 cgctatgct                                                           9
```